(12) United States Patent
Morales et al.

(10) Patent No.: US 11,654,166 B2
(45) Date of Patent: *May 23, 2023

(54) **THERAPEUTIC BACTERIOPHAGE COMPOSITIONS FOR TREATING *STAPHYLOCOCCUS* INFECTION**

(71) Applicant: Armata Pharmaceuticals, Inc., Marina del Rey, CA (US)

(72) Inventors: Sandra P. Morales, Sydney (AU); Gillian Mearns, Sydney (AU); Deborah A. Rankin, Sydney (AU); Frenk Smrekar, Ljubjlana (SI)

(73) Assignee: ARMATA PHARMACEUTICALS, INC., Marina del Rey, CA (US)

( * ) Notice: Subject to any disclaimer, the term of this patent is extended or adjusted under 35 U.S.C. 154(b) by 199 days.

This patent is subject to a terminal disclaimer.

(21) Appl. No.: 16/959,666

(22) PCT Filed: Jan. 2, 2019

(86) PCT No.: PCT/US2019/012114
§ 371 (c)(1),
(2) Date: Jul. 1, 2020

(87) PCT Pub. No.: WO2019/136109
PCT Pub. Date: Jul. 11, 2019

(65) Prior Publication Data
US 2021/0077551 A1    Mar. 18, 2021

Related U.S. Application Data

(60) Provisional application No. 62/731,775, filed on Sep. 14, 2018, provisional application No. 62/678,611, filed on May 31, 2018, provisional application No. 62/613,050, filed on Jan. 2, 2018.

(51) Int. Cl.
| | | |
|---|---|---|
| A61K 35/76 | (2015.01) | |
| A61P 31/14 | (2006.01) | |
| A61K 9/00 | (2006.01) | |
| A61K 45/06 | (2006.01) | |

(52) U.S. Cl.
CPC ............ *A61K 35/76* (2013.01); *A61K 9/0019* (2013.01); *A61P 31/14* (2018.01); *A61K 45/06* (2013.01)

(58) Field of Classification Search
None
See application file for complete search history.

(56) References Cited

U.S. PATENT DOCUMENTS

| | | |
|---|---|---|
| 8,388,946 B2 | 3/2013 | Soothill et al. |
| 8,475,787 B2 | 7/2013 | Harper |
| 9,623,058 B2 | 4/2017 | Jia |
| 10,517,908 B2 | 12/2019 | Shaw et al. |
| 11,253,557 B2 | 2/2022 | Shaw et al. |
| 2011/0182863 A1* | 7/2011 | Jia .......................... A61L 15/46 424/93.6 |
| 2015/0216179 A1 | 8/2015 | Jia |
| 2017/0065649 A1 | 3/2017 | Shaw |
| 2018/0289756 A1 | 10/2018 | Harper et al. |
| 2019/0359947 A1 | 11/2019 | Shaw et al. |
| 2020/0171108 A1 | 6/2020 | Shaw et al. |

FOREIGN PATENT DOCUMENTS

| | | |
|---|---|---|
| JP | 2007259856 A | 10/2007 |
| JP | 2015512384 A | 4/2015 |
| JP | 2020520980 A | 7/2020 |
| WO | 9603649 A1 | 2/1996 |
| WO | WO 2005009451 | 2/2005 |
| WO | WO 2008110840 | 9/2008 |
| WO | WO 2009044163 | 4/2009 |
| WO | 2013141730 A1 | 9/2013 |
| WO | WO 2013164640 | 11/2013 |
| WO | 2016066722 A2 | 5/2016 |
| WO | 2017015652 A1 | 1/2017 |
| WO | WO 2018146437 | 8/2018 |

OTHER PUBLICATIONS

International Search Report and Written Opinion received for PCT Application No. PCT/GB2017/050376, dated Sep. 15, 2017, 12 pages.
Trial Registered on ANZCTR, Australian New Zealand Clinical Trials Registry, 7 pages, last updated Dec. 14, 2016, retrieved Feb. 3, 2021.
Magiorakos et al. (Mar. 2012) "Multidrug-Resistant, Extensively Drug-Resistant and Pandrug-Resistant Bacteria: An International Expert Proposal For Interim Standard Definitions for Acquired Resistance", Clinical Microbiology and Infection, 18(3):268-281.
World Health Organization (Jan. 9, 2017) "International Clinical Trials Registry Platform, A phase 1 investigator initialed study to evaluate the safety, tolerability and preliminary effectiveness of AB-SA01 in patients with chronic rhinosinusitis associated with *Staphylococcus aureus* infection", 2 pages.
AmpliPhi Biosciences Corporation, AmpliPhi Biosciences reports favorable final results from Phase 1 Trial of AB-SA01 in chronic rhinosinusitis, 2016, 5 pages.
Baker et al., Protein Structure Predication and Structural Genomics, Science, 2001, pp. 93-96, vol. 294, No. 5540.
Barr, et al., Value of charcoal media for recovering staphylococci incorporated in mupirocin ointment, Journal of clinical pathology, 1987, pp. 372-376, vol. 40, No. 4.
Bautz, Aphb: Early signs of efficacy seen in Phase 1 Trial of AB-SA01 in chronic rhinosinusitis, 2016, 4 pages.

(Continued)

*Primary Examiner* — Michelle F. Paguio Frising
*Assistant Examiner* — Grant C Currens
(74) *Attorney, Agent, or Firm* — Mintz, Levin, Cohn, Ferris, Glovsky and Popeo, P.C.

(57) ABSTRACT

The present disclosure relates to a bacteriophage composition comprising one or more (suitably two or more, or three) obligately lytic bacteriophages capable of infecting and lysing *Staphylococcus aureus*, and use of the same for treating *Staphylococcus aureus* bacterial infections.

34 Claims, 4 Drawing Sheets
Specification includes a Sequence Listing.

(56) References Cited

OTHER PUBLICATIONS

Bautz, et al., Safety of AB-SA01 firmly established following Phase 1 Trials, 2016, 3 pages.
Carlson, Appendix: Working with Bacteriophages: and Methodological Approaches, 58 pages, 2005 CRC Press.
Darling, et al., Mauve: Multiple Alignment of Conserved Genomic Sequence With Rearrangements, Genome Res., 2004, pp. 1394-1403, vol. 14, No. 7.
Hyman, et al., Practical methods for determining phage growth parameters, Bacteriophages. Humana Press, 2009, pp. 175-202.
Kelly, et al., Development of a broad-host-range phage cocktail for biocontrol, Bioengineered bugs 2.1, 2011, pp. 31-37.
Lehman, et al., Design and Preclinical Development of a Phage Product for the Treatment of Antibiotic-Resistant *Staphylococcus aureus* Infections, Viruses, 2019, 16 pages, vol. 11, No. 88.
Ooi, et al., A Phase 1 investigator initiated study to evaluate the safety, tolerability, and preliminary effectiveness of AB-SA01 in patients with chronic rhinosinusitis associated with *Staphylococcus aureus* infection, Internnationa; clinical trials registry platform, 2016, 3 pages.
Otter, et al., Molecular epidemiology of community-associated meticillin-resistant *Staphylococcus aureus* in Europe, Lancet, 2010, pp. 227-239, vol. 10, No. 4.
Shaw, et al., Efficacy of a bacteriophage cocktail in a *Staphylococcus aureus* mouse pneumonia model is comparable to Vancomycin, 2017, 1 page.
Thompson, et al., improving the sensitivity of progressive multiple sequence alignment through sequence weighting, position-specific gap penalties and weight matrix choice, Nucleic acids research, 1994, pp. 4673-4680.
Van Walle, et al., Align-m-a new algorithm for multiple alignment of highly divergent sequences, Bioinformatics 2004, pp. 1428-1435.
Zhang, et al., Bacteriophage effectively kills multidrug resistant *Staphylococcus aureus* clinical isolates from chronic rhinosinusitis patients, Int Forum Allergy Rhinol, 2018, pp. 406-414, vol. 8, No. 3.
Attwood, Teresa K. (Oct. 27, 2000) "The Babel of Bioinformatics", Science, 290(5491):471-473.
Kirby, Amy E. (Nov. 2012) "Synergistic Action of Gentamicin and Bacteriophage in a Continuous Culture Population of *Staphylococcus aureus*", PLoS One, 7(11):e51017(9 pages).
Ali et al. (2015) "Efficacy of Bacteriophage-Antibiotic Combinations against *Staphylococcus aureus* Infections: In vitro Study", International Journal of Pharmaceutical Sciences Review and Research, 34(1):186-189.
Alves et al. (Nov. 2014) "Combined use of Bacteriophage K and a Novel Bacteriophage to Reduce *Staphylococcus aureus* Biofilm", Applied and Environmental Microbiology, 80(21):6694-6703.
Drilling et al. (Jan.-Feb. 2014) "Bacteriophage Reduces Biofilm of *Staphylococcus aureus* Ex Vivo Isolates from Chronic Rhinosinusitis Patients", American Journal of Rhinology & Allergy, 28(1):3-11.
Ryan et al. (2011) "Recent Advances in Bacteriophage Therapy: How Delivery Routes, Formulation, Concentration and Timing Influence the Success of Phage Therapy", Journal of Pharmacy and Pharmacology, 63:1253-1264.

\* cited by examiner

FIG. 4

| | Sa83 | Sa87 | J-Sa36 | Sa38 | Sa41 | Sa42 | Sa44 | Sa51 | Sa76 | Sa81 | J-Sa37 |
|---|---|---|---|---|---|---|---|---|---|---|---|
| Sa83 | 100% (0%) | 96.7% (3.1%) | 96.0% (2.9%) | 97.9% (2.0%) | 99.8% (0.2%) | 99.9% (0.1%) | 97.7% (2.2%) | 97.9% (2.0%) | 97.4% (2.5%) | 97.9% (2.0%) | very low |
| Sa87 | | 100% (0%) | 93.3% (5.3%) | 94.9% (4.9%) | 96.7% (3.1%) | 96.8% (3.9%) | 94.7% (5.1%) | 94.9% (4.9%) | 94.4% (5.4%) | 94.9% (4.9%) | very low |
| J-Sa36 | | | 100% (0%) | 94.2% (4.7%) | 95.9% (3.0%) | 96.0% (2.9%) | 94.2% (4.9%) | 94.2% (4.7%) | 93.8% (5.2%) | 94.2% (4.7%) | very low |
| Sa38 | | | | 100% (0%) | 97.9% (2.0%) | 98.0% (2.0%) | 99.7% (0.3%) | 99.9% (0.0%) | 99.4% (0.6%) | 99.9% (0.1%) | very low |
| Sa41 | | | | | 100% (0%) | 99.8% (0.1%) | 97.7% (2.3%) | 97.9% (2.0%) | 97.4% (2.5%) | 97.9% (2.0%) | very low |
| Sa42 | | | | | | 100% (0%) | 96.8% (2.2%) | 98.0% (2.0%) | 97.5% (2.5%) | 98.0% (2.0%) | very low |
| Sa44 | | | | | | | 100% (0%) | 99.6% (0.3%) | 99.1% (0.9%) | 99.7% (0.3%) | very low |
| Sa51 | | | | | | | | 100% (0%) | 99.4% (0.6%) | 100.0% (0.0%) | very low |
| Sa76 | | | | | | | | | 100% (0%) | 99.4% (0.6%) | very low |
| Sa81 | | | | | | | | | | 100% (0%) | very low |
| J-Sa37 | | | | | | | | | | | 100% (0%) |

THERAPEUTIC BACTERIOPHAGE COMPOSITIONS FOR TREATING *STAPHYLOCOCCUS* INFECTION

CROSS REFERENCED APPLICATIONS

This application claims priority to U.S. Provisional Application No. 62/613,050 filed Jan. 2, 2018, U.S. Provisional Application No. 62/678,611 filed May 31, 2018, and U.S. Provisional Application No. 62/731,775 filed Sep. 14, 2018, the entirety of which is incorporated by reference herein.

SEQUENCE LISTING

The instant application contains a Sequence Listing, which has been submitted electronically in ASCII format and is hereby incorporated by reference in its entirety. Said ASCII copy, created on Jan. 2, 2019 is named 054249-502001WO_Sequence_Listing_ST25 and is 1,852,409 bytes in size.

BACKGROUND

Described herein are bacteriophage, compositions of bacteriophage, and use of the same for medical and non-medical applications.

The increasing number of human pathogens that are resistant to antibiotics has created an urgent need for new treatments for serious bacterial infections. Novel approaches that circumvent traditional mechanisms of antibiotic resistance, can be effective against biofilms, and avoid disruption of the native gut flora are especially desirable. This clinical challenge has sparked renewed interest in bacteriophage (phage) therapy.

SUMMARY

Provided herein are bacteriophage, including non-naturally occurring bacteriophage, bacteriophage compositions. The compositions can be substantially free of bacterial components such as bacterial endotoxin and host cell components (e.g., protein). The compositions can include one or more obligately lytic bacteriophages and optionally a cryoprotectant or other excipient. In some aspects, the bacteriophage includes a nucleic acid sequence, or has a genome that can include a nucleotide sequence, having at least 93% identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In some embodiments the sequence does not have 100% sequence identity to one or more SEQ ID NOS: 1-10. In some cases, each individual bacteriophage is not prone to generalized transduction and/or does not carry antibiotic resistance genes. In some embodiments, one or more of the bacteriophage are not naturally occurring.

In an aspect, provided herein are bacteriophage compositions substantially free of bacterial components such as bacterial endotoxin, bacterial host protein, and the like. In some embodiments, provided herein are bacteriophage compositions that include one or more obligately lytic bacteriophages capable of complementation. The bacteriophage can include a nucleic acid, or a genome, including a nucleotide sequence having at least 93% identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10, and optionally a cryoprotectant, In some embodiments the nucleotide sequence is not 100% identical to at least one of SEQ ID NO: 1, SEQ ID NO: 2, SEQ ID NO: 3 SEQ ID NO: 4, SEQ ID NO: 5, SEQ ID NO: 6, SEQ ID NO: 7, SEQ ID NO: 8, SEQ ID NO: 9, or SEQ ID NO: 10. In some embodiments, the composition's target bacteria range is broader than the range of any individual bacteriophage in the composition or the sum of the individual bacteriophage in the composition. In some embodiments, one or more of the bacteriophage in the compositions are not naturally occurring.

In an aspect, provided herein are bacteriophage compositions. The compositions can be substantially free of bacterial components, such as bacterial endotoxin, bacterial host protein, and the like. The compositions can include at least one obligately lytic bacteriophage. In some embodiments, the composition includes a storage media for storage at a temperature selected at or below 8° C. Any bacteriophage in the composition may include a nucleic acid, or have a genome, including a nucleotide sequence having at least 93% identity to one or more of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In some embodiments at least one bacteriophage nucleic acid or genome does not have 100% identity to any one of SEQ ID NOS: 1-10. At least one of the individual bacteriophage is not prone to generalized transduction and/or does not carry antibiotic resistance genes. In some embodiments, one or more of the bacteriophage of the compositions are not naturally occurring.

In another aspect, there is provided a bacteriophage composition for use as a medicament, or for use in the treatment of a bacterial illness associated with *S. aureus*. Any of the compositions provided herein are contemplated for use in the treatment of a disease or illness such as a *S. aureus* infection. In some embodiments, one or more of the bacteriophage are not naturally occurring. Corresponding methods of treating a disease comprising administration of the bacteriophage composition to a subject are also provided.

In an aspect, provided herein are methods of treating a human with a bacterial infection including administration to the human a composition including one or more distinct bacteriophages that infect and lyse *Staphylococcus aureus* bacteria. At least one of the bacteriophage can have a nucleic acid or a genome, including a polynucleotide sequence selected from one or more of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or a sequence having at least 93% identity to any one of SEQ ID NOS: 1-10. In some aspects one or more of the bacteriophage are not naturally occurring. The methods can include selecting a patient with a *S. aureus* infection. In some aspects, the infection is non-pulmonary.

In an aspect, provided herein are methods of treating a human with a confirmed non-pulmonary *S. aureus* infection including administration to the human of a composition including one or more distinct bacteriophage that infect and lyse *Staphylococcus aureus*. At least one of the bacteriophage include a nucleic acid a genome, comprising a nucleotide sequence selected from one or more of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or a sequence having at least 93% identity to any one of SEQ ID NOS: 1-10. In some aspects, the infection is not a pulmonary *S. aureus* infection. In some aspects one or more of the bacteriophage are not naturally occurring. The methods can include selecting a patient with a *S. aureus* infection. In some aspects, the infection is non-pulmonary.

In an aspect, provided herein are methods of modifying the microbial flora in a human including administering to said human a composition including one or more distinct bacteriophages having lytic activity against *Staphylococcus aureus*. The one or more distinct bacteriophages are selected from bacteriophages having nucleic acid or a genome, including a nucleotide sequence of any one of SEQ ID NO: 1, SEQ ID NO:2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or a sequence having at least 93% identity to any one of SEQ ID NOS: 1-10. In some aspects one or more of the bacteriophage are not naturally occurring. The methods can include selecting a patient with a *S. aureus* infection. In some aspects, the infection is non-pulmonary.

A further aspect relates to, for example, a bacteriophage composition for use in treating a bacterial infection in a subject, wherein the bacteriophage composition is administered to the subject, and wherein the bacterial infection includes *Staphylococcus* (e.g., *Staphylococcus aureus*) infections.

Some aspects relate to, for example, use of a bacteriophage composition in the manufacture of a medicament for use in treating a bacterial infection in a subject, wherein the bacteriophage composition is administered to the subject, and wherein the bacterial infection comprises *Staphylococcus* (e.g., *Staphylococcus aureus*).

Some aspects relate to a bacteriophage. For example, a bacteriophage designated herein as Sa87, J-Sa36, Sa83, Sa38, Sa41, Sa42, Sa44, Sa51, Sa76, and Sa81. Also, a bacteriophage having 90-100% nucleic acid sequence identity to any of the same and/or to one or more of SEQ ID NOs: 1-10.

Some aspects relate to uses of any bacteriophage or composition described herein in the treatment of a *Staphylococcus aureus* infection in a human, wherein the infection is substantially or completely non-pulmonary. The use can include administering the composition to a human suffering from a *S. aureus* infection.

Some aspects relate to uses of any bacteriophage or composition described herein in the treatment of a *Staphylococcus aureus* infection in a human. The uses can include, for example, administering a composition of one or more distinct bacteriophages to said human; wherein at least one of said one or more bacteriophage comprises a genome comprising a polynucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and a sequence having at least 93% identity to any one of SEQ ID NOS: 1-10. In some uses, the one more of the bacteriophage are not naturally occurring.

Some aspects relate to uses of any bacteriophage or composition described herein in the treatment of a confirmed non-pulmonary *Staphylococcus aureus* infection in a human. The uses can include the treatment comprising administration to said human of a composition, the composition comprising at least two bacteriophages comprising a nucleic acid or a genome that includes a nucleotide sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10 and a sequence having at least 93% identity to any of SEQ ID NOS: 1-10, wherein the infection is not a pulmonary *S. aureus* infection. In some uses, the one more of the bacteriophage are not naturally occurring.

BRIEF DESCRIPTION OF THE DRAWINGS

Embodiments will now be described, by way of example only, with reference to the accompanying drawings, in which:

FIG. 4 is a summary chart showing phage candidates' single-copy nucleic acid similarities are shown in (% nucleotide identity). Within each cell, values are percent identity across the total alignment. The percent of the alignment made up by gaps is reported separately in parentheses by these gaps are included in the total percent identity.

DETAILED DESCRIPTION

Figure 1:
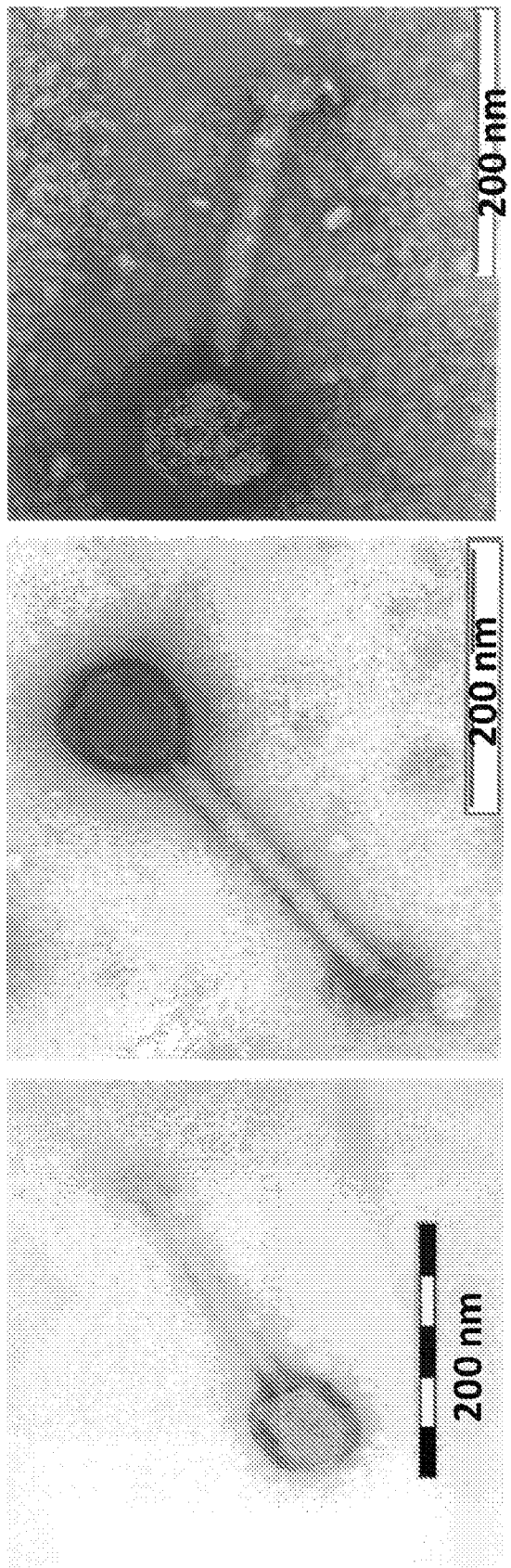
FIGS. 1A, 1B, and 1C shows transmission electron microscopy (TEM) images of examples of three component bacteriophage Sa83 (FIG. 1A), Sa87 (FIG. 1B), and J-Sa36 (FIG. 1C). The images show the straight contractile tail and narrow neck that are characteristic of phages belonging to the order Caudovirales, family Myoviridae.

It is to be understood that the present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

The detailed description of the present disclosure is divided into various sections only for the reader's convenience and disclosure found in any section may be combined with that in another section. Unless defined otherwise, all technical and scientific terms used herein have the same meaning as commonly understood by one of ordinary skill in the art to which the present disclosure belongs.

Definitions

It must be noted that as used herein and in the appended claims, the singular forms "a," "an," and "the" include plural referents unless the context clearly dictates otherwise. Thus, for example, reference to "a bacteriophage composition" includes a plurality of such candidate agents and reference to "the bacteriophage" includes reference to one or more bacteriophages and equivalents thereof known to those skilled in the art, and so forth.

As used herein, the term "about" when used before a numerical designation, e.g., temperature, time, amount, concentration, and such other, including a range, indicates approximations which may vary by (+) or (−) 10%, 5%, or 1%.

When a range (e.g., dosage range) is listed herein, it is to be understood that the value may include any individual value or range within the recited range(s), including endpoints.

The term "mutant" as used herein refers to a bacteriophage differing genetically from Sa87, J-Sa36, or Sa83 but still retaining the ability to infect and lyse *Staphylococcus aureus* target bacteria. Mutants typically comprise e.g., silent mutations, conservative mutations, minor deletions, and/or minor replications of genetic material, and retain phenotypic characteristics of the reference bacteriophage. In an embodiment, the mutants retain any observable characteristic or property that is dependent upon the genome of the bacteriophage as described herein, i.e. phenotypic characteristics of said bacteriophage and/or lytic activity against *Staphylococcus* species. Preferred mutants retain the ability to infect and lyse *Staphylococcus aureus* target bacteria and have less than 10% nucleic acid variation as compared to the genome of the reference bacteriophage, even more preferably less than 7%, more preferably less than 1%. Alternatively, or in combination, mutants have preferably less than 7% amino acid variation in a coded polypeptide sequence as compared to a polypeptide of the reference bacteriophage. Examples of phage that have less than 10% nucleic acid variation across the entire genome when compared to any one of Sa87, J-Sa36, or Sa83 and had lytic activity against *Staphylococcus aureus* target bacteria include Sa38, Sa41, Sa42, Sa44, Sa51, Sa76, and Sa81 (FIG. 4).

The term "% identity" or "% sequence identity" in relation to nucleic acid or amino acid sequences designates the level of identity or homology between said sequences and may be determined by techniques known in the art. Any of a variety of sequence alignment methods can be used to determine percent identity, including, without limitation, global methods, local methods and hybrid methods, such as segment approach methods. Protocols to determine percent identity are routine procedures within the scope of one skilled in the art. Global methods align sequences from the beginning to the end of the molecule and determine the best alignment by adding up scores of individual nucleotide pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement. Non-limiting methods include, e.g., BLAST, Match-box, see, e.g., Align-M, see, e.g., Ivo Van Walle et al., Align-M—A New Algorithm for Multiple Alignment of Highly Divergent Sequences, Bioinformatics 20(9):1428-1435 (2004). This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 100 nucleotides in length, or more preferably over a region that is 100-1000 or more nucleotides in length.

The term "complementation" as used herein refers to the ability of a bacteriophage with a particular genome to compensate for a different, distinct bacteriophage with a different genome. More specifically, bacteriophage insensitive mutants colonies (of target bacteria) may arise to a particular bacteriophage but may still be sensitive to a different bacteriophage. In other words, bacteriophage resistant mutant bacteria arising to one phage are still sensitive to another phage.

The term "generalized transduction" as used herein refers process by which any bacterial DNA may be transferred to another bacterium via a bacteriophage. It is a rare event; a very small percentage of phage particles happen to carry a donor bacterium's DNA, on the order of 1 phage in 10,000. In essence, this is the packaging of bacterial DNA into a viral envelope.

The term "treat" or "treating" as used herein is intended to encompass prophylactic treatment as well as corrective treatment (treatment of a subject already suffering from a disease).

The term "lytic" or "lytic activity" designates the property of a bacteriophage to cause lysis of a bacterial cell. The lytic activity of a bacteriophage can be tested on a bacteria (e.g., *S. aureus* strains) according to techniques known in the art. The lytic cycle is named for the process that occurs when a phage has infected a cell, replicated new phage particles, and bursts through the host cell membrane. Some phage exhibit a lysogenic cycle during which the bacteriophage DNA remains practically dormant due to active repression of bacteriophage processes. Whenever the bacteria divides, the DNA of the phage is copied as well. In this way, the virus can continue replicating within its host without lysing the host. At a certain point, conditions may change and the phage enters a lytic cycle. "Obligately lytic" refers to phage that are unable to undergo a lysogenic cycle.

A use or method typically comprises administering a bacteriophage or bacteriophage composition described herein to a subject. As used herein, a "subject" is a mammal, such as a human or other animal. Preferably, the subject is a human.

The term "isolated" as used herein indicates that the bacteriophage are removed from its original environment in which it naturally occurs. In particular, an isolated bacteriophage is, e.g., cultivated, cultured separately from the environment in which it is naturally located.

The term "purified" as used herein indicates that the bacteriophage are removed from manufacturing host bacteria. In particular, a purified bacteriophage has production impurities, such as bacterial components, removed from its manufacturing or production environment. Bacterial components include but are not limited to bacterial host proteins, lipids, and/or bacterial endotoxin. The term "purified" may also refer to genetic purification in which the strain of bacteriophage is genetically homogenous.

As used herein, the term "substantially purified" refers to a composition containing less than 1%, less than 0.1%, less than 0.001%, or no detectable amount of contaminants such as host bacterial proteins or endotoxin. Also, as used herein, the term "substantially pure" when used to describe a bacteriophage strain refers to the genetic purity of the composition such that the strain is greater than 99%, greater than 99.9%, greater than 99.999%, or 100% of one particular genome sequence.

Typically, a composition is substantially pure when at least 80%, at least 85%, at least 90%, at least 95%, at least 98%, or at least 99% of the total material (by volume, by wet or dry weight, or by mole percent or mole fraction) in a sample is free of impurities or genetic variants.

The term "subject" or "patient" refers to a human or non-human animal. Preferably, the subject or patient is in need of treatment with the composition as described herein, e.g., has a bacterial infection susceptible to treatment with the composition.

A "synergistic amount" as used herein refers to the sum of a first amount (e.g., a bacteriophage) and a second amount (e.g., a different bacteriophage) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent.

The term "substantially free" as used herein can refer to something having less than 10% of the substance that it is to be free from. For example, 0.01% to 10% free, including any subvalue and subrange therein. For example, 0.01, 0.02, 0.03, 0.04, 0.05, 0.06, 0.07, 0.08, 0.09, 1, 2, 3, 4, 5, 6, 7, 8, 9, or 10%.

Additional terms and phrases are defined below.

Bacteriophage Compositions

Provided herein are bacteriophage compositions, including compositions that are substantially free of bacterial components such as for example bacterial endotoxins, bacterial host protein, and the like. The compositions can include one or more obligately lytic bacteriophages and optionally a cryoprotectant. The bacteriophage can be any phage as described herein, include at least one phage with a nucleic acid sequence or a genome including a nucleotide sequence having at least 93% identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In some aspects at least one of the bacteriophage do not have 100% identity to one or more of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10. In some aspects one or more of the bacteriophage are non-naturally occurring. In some aspects an individual bacteriophage is not prone to generalized transduction and/or does not carry antibiotic resistance genes.

In embodiments, the bacteriophage differ in nucleotide or genomic sequence by up to about 10%, up to about 9%, up to about 8%, up to about 7%, up to about 6%, up to about 5%, up to about 4%, up to about 3%, up to about 2% or up to about 1% compared to the genomic sequence of Sa87 (SEQ ID NO.: 1), J-Sa36 (SEQ ID NO.: 2), and/or Sa83 (SEQ ID NO.: 3). Examples of phage that have less than 10% nucleic acid variation across the entire genome when compared to any one of Sa87, J-Sa36, or Sa83 and had lytic activity against *Staphylococcus aureus* target bacteria include Sa38 (SEQ ID NO.: 4), Sa41 (SEQ ID NO.: 5), Sa42 (SEQ ID NO.: 6), Sa44 (SEQ ID NO.: 7), Sa51 (SEQ ID NO.: 8), Sa76 (SEQ ID NO.: 9), and Sa81 (SEQ ID NO.: 10) (FIG. 4). In some aspects one or more of the bacteriophage, compositions of bacteriophage, and methods of uses include one or more bacteriophage that have a nucleic acid having a sequence that is 90%-99.99% identity 90%, 91%, 92%, 93%, 94%, 95%, 96%, 97%, 98%, 99%, 99.9% or 100% identity to one or more of SEQ ID NOs. 1-10, or to a nucleic acid sequence of Sa87, J-Sa36, Sa83, Sa38, Sa41, Sa42, Sa44, Sa51, Sa76, and Sa81. In some aspects one or more of the bacteriophage are non-naturally occurring while in others one or more phage are naturally occurring. In one embodiment, the bacteriophage composition includes one or more additional bacteriophage. The bacteriophages disclosed herein and mutants thereof are useful for treating a bacterial infections, in particular a *Staphylococcus aureus* infection.

The bacteriophages Sa87 (deposited under ECACC reference no. 17020901), J-Sa36 (deposited under ECACC reference no. 17020903), and Sa83 (deposited under ECACC reference no. 17020902) were deposited at the European Collection of Cell Cultures (ECACC), Culture Collections, Public Health England, Porton Down, Salisbury, Wiltshire, SP4 0JG, United Kingdom, on 9 Feb. 2017. All of the deposits were made under the provisions of the Budapest Treaty on the International Recognition of the Deposit of Microorganisms for the Purposes of Patent Procedure.

In an aspect, provided herein are bacteriophage compositions substantially free of bacterial components including bacterial endotoxins and bacterial host protein. In some embodiments the compositions can include one or more obligately lytic bacteriophages capable of complementation. The bacteriophage can have a nucleic acid sequence or a genome, that include a nucleotide sequence having at least 93% but not 100% identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, and a cryoprotectant, The composition's target bacteria range can be broader than the range of any individual bacteriophage or the phage collectively in the composition, or have an effectiveness that is greater than the sum of effectiveness of the individual bacteriophage. The compositions can have at least one bacteriophage that is not naturally occurring. The compositions can include at least one naturally occurring phage or can exclude naturally occurring phage.

In an aspect, provided herein are bacteriophage compositions substantially free of bacterial components such as bacterial endotoxin, bacterial host protein, and the like. The bacteriophage compositions may include at least one obligately lytic bacteriophage and optionally a storage media for storage at a temperature selected at or below 8° C. The bacteriophage can include a nucleic acid or a genome, that includes a nucleotide sequence having at least 93% but not 100% identity to any one of SEQ ID NO: 1, SEQ ID NO: 2, SEQ ID NO: 3 SEQ ID NO: 4, SEQ ID NO: 5, SEQ ID NO: 6, SEQ ID NO: 7, SEQ ID NO: 8, SEQ ID NO: 9, SEQ ID NO: 10. One or more individual bacteriophage may not be prone to generalized transduction and does not carry antibiotic resistance genes. The compositions can have at least one bacteriophage that is not naturally occurring. The compositions can include at least one naturally occurring phage or can exclude naturally occurring phage.

In embodiments, a bacteriophage composition includes at least one bacteriophage having nucleic acid or genomic nucleic acid sequences having at least 93%, but not 100%, identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10. In embodiments, a bacteriophage composition includes at least two bacteriophages having nucleic acid or genomic nucleic acid sequences having at least 93%, but not 100%, identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10. In embodiments, a bacteriophage composition includes at least three bacteriophages having nucleic acid or genomic nucleic acid sequences having at least 93%, but not 100%, identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10. In another embodiment a bacteriophage composition includes bacteriophage having at least 93%, but not 100%, identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10. In embodiments, a bacteriophage composition consists essentially of bacteriophage having nucleic acid or genomic nucleic acid sequences having at least 93%, but not 100%, identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10. A bacteriophage composition including two or more bacteriophages may be referred to herein as a "panel" of bacteriophages. In some embodiments where the composition includes one or more bacteriophage that do not have 100% identity to one or more of SEQ ID NOs: 1-10, the compositions can include at least one bacteriophage that does have 100% identity. The compositions can have at least one bacteriophage that is not naturally occurring. The compositions can include at least one naturally occurring phage or can exclude naturally occurring phage.

In embodiments, a bacteriophage composition includes one or more bacteriophages having nucleic acid or genomic nucleic acid sequences having at least 93%, but not 100%, identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10. In embodiments, a bacteriophage composition includes two or more bacteriophages having genomic nucleic acid sequences having at least 93% but not 100% identity to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10. In embodiments, a bacteriophage composition includes three or more bacteriophage having at least 93% but not 100% identity to any one of SEQ ID NO: 1, SEQ ID NO: 2, SEQ ID NO: 3 SEQ ID NO: 4, SEQ ID NO: 5, SEQ ID NO: 6, SEQ ID NO: 7, SEQ ID NO: 8, SEQ ID NO: 9, SEQ ID NO: 10. The compositions can have at least one bacteriophage that is not naturally occurring. The compositions can include at least one naturally occurring phage or can exclude naturally occurring phage.

In embodiments, the bacteriophage composition can be an alternative to conventional antibacterial agents/therapeutics, and overcomes one or more problems associated therewith. In some aspects, the bacteriophage composition can be utilized as co-treatment or in combination with conventional antibacterial agents/therapeutics. In some aspects the methods herein can include the use of the bacteriophage and compositions described herein to treat a patient that has already been treated for his/her infection with another therapy such as an antibiotic treatment. The patient can be identified and/or selected for the method based upon having received such prior treatment, including a prior treatment where the infection was not completely eliminated or where the infection persists. In other aspects the patient can be selected due to being one that has not received another prior treatment.

In embodiments, the bacteriophage composition can include one or more additional bacteriophages. In a preferred embodiment, the one or more additional bacteriophages are suitable for treating a bacterial infection, in particular a *Staphylococcus* infection. The additional one or more phage can be natural or non-naturally occurring. The one or more additional phage can be a phage with 90%-100% nucleic acid sequence identity to any of the phage described herein, including phage associated with SEQ ID NOs: 1-10.

The term "consists essentially of" as used herein means that only the bacteriophage(s) explicitly indicated are present in the bacteriophage composition, but that said composition may also contain a further non-bacteriophage constituent, such as an appropriate carrier, diluent, antibiotic (e.g., chemical antibiotic), etc.

In an aspect, the bacteriophage composition includes at least one, at least two, or at least three bacteriophages such that the composition is effective against at least about 60% of target bacterial strains. For example, the bacteriophage composition is effective against (e.g., kills or lyses) at least 60% of *Staphylococcus aureus* strains in a given panel. In one embodiment, the bacteriophage composition includes at least one, at least two, or at least three bacteriophages such that the composition is effective against at least about 70% of target bacterial strains. In one embodiment, the bacteriophage composition includes at least one, at least two, or at least three bacteriophages such that the composition is effective against at least about 75% of target bacterial strains. In one embodiment, the bacteriophage composition includes at least one, at least two, or at least three bacteriophage such that the composition is effective against at least about 76% of target bacterial strains. In one embodiment, the bacteriophage composition includes at least one, at least two, or at least three bacteriophages such that the composition is effective against at least about 77% of target bacterial strains. In one embodiment, the bacteriophage composition comprises at least one, at least two, or at least three bacteriophages such that the composition is effective against at least about 78% of target bacterial strains. In one embodiment, the bacteriophage composition includes at least one, at least two, or at least three bacteriophages such that the composition is effective against at least about 79% of target bacterial strains. In one embodiment, the bacteriophage composition includes at least one, at least two, or at least three bacteriophages such that the composition is effective against at least about 80% of target bacterial strains. In one embodiment, the bacteriophage composition includes at least one, at least two, or at least three bacteriophages such that the composition is effective against at least about 81% of target bacterial strains. In one embodiment, the bacteriophage composition includes at least one, at least two, or at least three bacteriophages such that the composition is effective against at least about 82% of target bacterial strains. In one embodiment, the bacteriophage composition includes at least one, at least two, or at least three r bacteriophage such that the composition is effective against at least about 83% of target bacterial strains. In one embodiment, the bacteriophage composition includes at least one, at least two, or at least three bacteriophages such that the composition is effective against at least about 84% of target bacterial strains. In one embodiment, the bacteriophage composition includes at least one, at least two, or at least three bacteriophage such that the composition is effective against at least about 85% of target bacterial strains. In one embodiment, the bacteriophage composition includes at least one, at least two, or at least three bacteriophage such that the composition is effective against at least about 90% of target bacterial strains. In another embodiment, the bacteriophage composition includes at least one, at least two, or at least three bacteriophages such that the composition is effective against one or more bacterial strains (or isolates) from a subject with a bacterial infection.

In embodiments, the range of target bacteria of the composition is broader than the range of target bacteria of any single bacteriophage included within the composition. Such activity can be considered synergistic as the effect of the composition (target killing range) is greater than the sum of individual effects (target killing range) of each component bacteriophage.

In one embodiment (alternatively or additionally) a "mutant" bacteriophage is capable of lysing some or all the same target bacterial strains as one or more of Sa87, J-Sa36, Sa83, Sa38, Sa41, Sa42, Sa44, Sa51, Sa76, and/or Sa81, and/or further capable of lysing one or more additional bacterial strains. In one embodiment, a mutant may have at least 90%, 91%, 92%, 93%, 94%, 95%, 96%, 97%, 98%, or 99% sequence identity to a nucleic acid sequence of one or more of Sa87, J-Sa36, Sa83, Sa38, Sa41, Sa42, Sa44, Sa51, Sa76, and Sa81. In some embodiments, a mutant or variant may have at least 90%, 91%, 92%, 93%, 94%, 95%, 96%, 97%, 98%, or 99% sequence identity across its entire genome when compared to one more of Sa87, J-Sa36, Sa83, Sa38, Sa41, Sa42, Sa44, Sa51, Sa76, and Sa81. In one embodiment, a mutant may have at least 93%, 94%, 95%, 96%, 97%, 98%, or 99% sequence identity across its entire genome when compared to SEQ ID NO.: 1, SEQ ID NO.: 2, SEQ ID NO.: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

In embodiments, a "mutant" may be a bacteriophage progeny. A bacteriophage progeny may be a bacteriophage obtainable after lysing *Staphylococcus* (e.g., *S. aureus*) target bacteria using a bacteriophage as described herein (i.e., the "parent bacteriophage"). In other words, the bacteriophage progeny may be a second (or further) generation bacteriophage.

In embodiments, a bacteriophage progeny is obtainable by contacting one or more bacteriophage(s) described herein, including for example, one selected from Sa87, J-Sa36, and/or Sa83 with a *Staphylococcus* target bacteria such that the one or more bacteriophage(s) infects and lyses the target bacteria; and obtaining a bacteriophage released following lysis of the target bacteria. The bacteriophage progeny will typically comprise one or more nucleotide(s) mutation(s) when compared to the relevant parent bacteriophage.

The term "obtainable" as used herein also encompasses the term "obtained." In one embodiment, the term "obtainable" means obtained.

The bacteriophage composition targets (and preferably kills) one or more *Staphylococcus* species or strain. In embodiments, the composition targets *Staphylococcus aureus*, including e.g. one or more strains of *Staphylococcus aureus*. In one embodiment, a *Staphylococcus* species or strain targeted by the bacteriophage is a *Staphylococcus* species or strain resistant to chemical antibiotics, such as a multi-drug resistant *Staphylococcus* species or strain. In one embodiment, a *Staphylococcus* species or strain targeted by the bacteriophage is a *Staphylococcus aureus* strain resistant to chemical antibiotics, such as a multi-drug resistant *Staphylococcus aureus*.

In embodiments, the bacteriophage compositions described herein have been shown to be particularly effective at treating *Staphylococcus* species or strain infections resistant to chemical antibiotics, such as a multi-drug resistant *Staphylococcus* species or strain. In embodiments, the bacteriophage compositions described herein have been shown to be particularly effective at treating *Staphylococcus aureus* infections resistant to chemical antibiotics, such as a multi-drug resistant *Staphylococcus aureus* strain.

The bacteriophages may be provided in the form of a single therapeutic composition (preferred) or as a number of separate compositions each comprising one or more members of the composition. In embodiments where the bacteriophages are provided in a number of separate compositions, said bacteriophages may be administered to a subject sequentially or simultaneously (suitably simultaneously).

In embodiments where more than one bacteriophage is present in the bacteriophage composition, the composition is formulated such that each bacteriophage may be present at a ratio of between 1:10 and 10:1 (or any sub value or subrange there between including the endpoints) compared to the amount (e.g., concentration) of any other bacteriophage in the composition. In embodiments, each bacteriophage is present at a ratio of about 1:1 compared to one or more other bacteriophages in the composition. In embodiments, each bacteriophage is present at a ratio of about 1:2 compared to one or more other bacteriophages in the composition. In embodiments, each bacteriophage is present at a ratio of about 1:3 compared to one or more other bacteriophages in the composition. In embodiments, each bacteriophage is present at a ratio of about 1:4 compared to one or more other bacteriophages in the composition. In embodiments, each bacteriophage is present at a ratio of about 1:5 compared to one or more other bacteriophages in the composition. In embodiments, each bacteriophage is present at a ratio of about 1:6 compared to one or more other bacteriophages in the composition. In embodiments, each bacteriophage is present at a ratio of about 1:7 compared to one or more other bacteriophages in the composition. In embodiments, each bacteriophage is present at a ratio of about 1:8 compared to one or more other bacteriophages in the composition. In embodiments, each bacteriophage is present at a ratio of about 1:9 compared to one or more other bacteriophages in the composition. In embodiments, each bacteriophage is present at a ratio of about 1:10 compared to one or more other bacteriophages in the composition. In embodiments, each bacteriophage is present at a ratio of about 10:1 compared to one or more other bacteriophages in the composition. In embodiments, each bacteriophage is present at a ratio of about 5:1 compared to one or more other bacteriophages in the composition. In embodiments, each bacteriophage is present at a ratio of about 10:3 compared to one or more other bacteriophages in the composition. In embodiments, each bacteriophage is present at a ratio of about 5:2 compared to one or more other bacteriophages in the composition. In embodiments, each bacteriophage is present at a ratio of about 2:1 compared to one or more other bacteriophages in the composition. In embodiments, each bacteriophage is present at a ratio of about 5:3 compared to one or more other bacteriophages in the composition. In embodiments, each bacteriophage is present at a ratio of about 10:7 compared to one or more other bacteriophages in the composition. In embodiments, each bacteriophage is present at a ratio of about 5:4 compared to one or more other bacteriophages in the composition.

A bacteriophage for inclusion in a composition may be propagated by any suitable method known in the art. For example, one or more bacteriophage(s) may be grown separately in host bacterial strains capable of supporting growth of the bacteriophage. Typically, the bacteriophage will be grown in said host bacterial strain to high concentrations, titrated and combined to form the composition. The amount of each bacteriophage employed (e.g., in a bacteriophage composition, method or use) will depend upon its virulence against the target bacterial species.

The amount of each bacteriophage employed (e.g. in a bacteriophage composition, method or use as described herein) may depend upon its virulence against the target bacterial isolate.

Count bacterial strains may be used in the development of a composition, i.e., bacterial strains which are indicators for individual prospective members of the composition (e.g. panel). A count strain may permit at least 1000 times more plaque formation by one prospective member of the bacteriophage composition than another. In this way, a composition (e.g. panel) that is consistently effective against a wide range of bacterial isolates may be achieved.

Typically, the one or more bacteriophage(s) may be combined to form a composition including at least about $1\times10^5$, $1\times10^6$, $1\times10^7$, $1\times10^8$, $1\times10^9$ or $1\times10^{10}$ or $1\times10^{11}$ plaque forming units (PFU) of each phage per ml of composition. The composition may include $1\times10^5$ to $1\times10^{11}$ PFU of each phage per ml of composition. In embodiments, the composition may include $1\times10^5$ to $1\times10^6$ PFU, $1\times10^5$ to $1\times10^7$ PFU, $1\times10^5$ to $1\times10^8$ PFU, $1\times10^5$ to $1\times10^9$ PFU, or $1\times10^5$ to $1\times10^{10}$ PFU of each phage per ml of composition. In embodiments, the composition may include $1\times10^6$ to $1\times10^7$ PFU, $1\times10^6$ to $1\times10^8$ PFU, $1\times10^6$ to $1\times10^9$ PFU, $1\times10^6$ to $1\times10^{10}$ PFU, or $1\times10^6$ to $1\times10^{11}$ PFU of each phage per ml of composition. In embodiments, the composition may include $1\times10^7$ to $1\times10^8$ PFU, $1\times10^7$ to $1\times10^9$ PFU, $1\times10^7$ to $1\times10^{10}$ PFU, or $1\times10^7$ to $1\times10^{11}$ PFU of each phage per ml of composition. In embodiments, the composition may include $1\times10^8$ to $1\times10^9$ PFU, $1\times10^8$ to $1\times10^{10}$ PFU, or $1\times10^8$ to $1\times10^{11}$ PFU of each phage per ml of composition. In embodiments, the composition may include $1\times10^9$ to $1\times10^{10}$ PFU or $1\times10^9$ to $1\times10^{11}$ PFU of each phage per ml of composition. In embodiments, the composition may include $1\times10^{10}$ to $1\times10^{11}$ PFU of each phage per ml of composition. In embodiments, one or more bacteriophage(s) may be combined to form a composition include $1\times10^5$, $1\times10^6$, $1\times10^7$, $1\times10^8$, $1\times10^9$ or $1\times10^{10}$, or $1\times10^{11}$ PFU of each phage per ml of composition. In some embodiments, the composition includes equal (or substantially equal) concentrations of each bacteriophage included herein. Suitable concentrations include any value or subrange within the indicated ranges, including endpoints.

In some aspects, the bacteriophage(s) in the composition are purified or substantially purified.

When selecting bacteriophages for inclusion in the composition, the methods include (a) providing two or more different bacteriophages, wherein each of said two or more different bacteriophages independently retards growth of a *Staphylococcus* species or strain under defined growth conditions; (b) combining at least two of said two or more different bacteriophages; and (c) determining growth of the *Staphylococcus* species or strain in the presence of said combination of two or more different bacteriophages, wherein the *Staphylococcus* species or strain growth conditions are the same or equivalent in steps (a) and (c); wherein, if said combination retards growth of the *Staphylococcus* species or strain at least equal to the greatest growth retardation achieved independently by any one of said two or more different bacteriophages, the combination is accepted as a composition of bacteriophages. In embodiments, if said combination retards growth of the target bacterial species or strain less than the greatest growth retardation achieved independently by any one of said two or more different bacteriophages, the combination is initially rejected as a composition of bacteriophages.

Provided herein is a bacteriophage composition including one or more of bacteriophages Sa87, J-Sa36 and Sa83 (and optionally mutants and identity variants thereof). The bacteriophage composition comprises or consists essentially of Sa87, J-Sa36 and Sa83. The bacteriophage composition comprises or consists essentially of bacteriophage(s) having a nucleotide genome sequence 90%-100% identical to a phage or phage sequence described herein. For example, in one aspect a bacteriophage composition can include or consist essentially of a phage having at least 93% but not 100% identical to the genome sequence of Sa87, J-Sa36 and Sa83 (or any other sequence described herein). In embodiments, only bacteriophage having a nucleotide genome sequence at least 93% identity to the genome sequence of Sa87, J-Sa36 and/or Sa83 are present in the composition. In some embodiments, the bacteriophage in the composition consist of bacteriophage having a nucleotide genome sequence at least 93% identity to the genome sequence of at least one of Sa87, J-Sa36 and/or Sa83, and no other (detectable) bacteriophage are present in the composition. In embodiments, the only bacteriophage present in the composition that target *S. aureus* are bacteriophage having a nucleotide genome sequence at least 93% identity to the genome sequence of Sa87, J-Sa36 and/or Sa83. In embodiments, the bacteriophage having a nucleotide genome sequence at least 93% identity to the genome sequence of Sa87, J-Sa36 and/or Sa83 do not have 100% identity to the genome sequence of Sa87, J-Sa36 and/or Sa83. In some embodiments, the composition includes at least one bacteriophage as described herein, or at least two, at least three or more. In some embodiments the compositions include one or more bacteriophage of Sa87, J-Sa36 and Sa83, and one or more other bacteriophage having at least 90-99% sequence identity to at least one of the same, or at least one other bacteriophage effective against S. *Aureus*.

In some embodiments, a bacteriophage composition may further comprise one or more additional bacteriophages. Said one or more additional bacteriophages may target a *Staphylococcus aureus* species or strain, or a different bacterial target, for example selected from one or more of the following genera *Staphylococcus, Helicobacter, Klebsiella, Listeria, Mycobacterium, Escherichia, Meningococcus, Campylobacter, Streptococcus, Enterococcus, Shigella, Pseudomonas* (e.g., *Pseudomonas aeruginosa*), *Burkholderia, Clostridium, Legionella, Acinetobacter, Salmonella,* or combinations thereof.

The one or more additional bacteriophages may be one taught in WO 2009/044163 (incorporated herein by reference in its entirety for all of its bacteriophage, compositions, composition components/excipients, and methods of use), a bacteriophage K and/or bacteriophage P68 described therein.

In some embodiments, the bacteriophage composition comprises one or more bacteriophage and a preservative agent for storage. Storage includes frozen, refrigeration, and room temperature storage. In one embodiment, the preservative agent is glycerol. In an embodiment, the preservative agent is present in the composition in an amount sufficient to preserve the composition, for example during storage in a freezer or ultra-freezer (e.g., at temperatures from about 0° C. to about −80° C., more preferably from about −20° C. to about −80° C., most preferably about −80° C.), or in liquid nitrogen. In another embodiment, the preservative agent is present in the composition in an amount sufficient to preserve the composition during long-term storage, e.g., in a freezer, ultra freezer, or liquid nitrogen. In one embodiment, the preservative agent is between about 5% and about 50% glycerol; more preferably between about 10% and about 30% glycerol; most preferably about 20% glycerol. Suitable concentrations may be any value or subvalue within the recited ranges, including endpoints.

Formulations

Provided herein are bacteriophage compositions that include or consist essentially of one more of the bacteriophage described herein. In some aspects the compositions can be substantially free of bacterial components, such as for example, bacterial endotoxin, bacterial host cell components and materials (e.g., protein), and the like. In some embodiments, the compositions can one or more obligately lytic bacteriophages. The one or more bacteriophage may include a nucleic acid, for example, a genome including a nucleotide sequence having 90%-100% identity to one or more of SEQ ID NOs: 1-10. In some embodiments, at least one or more phage have at least 93%, but not 100%, nucleic acid sequence identity to any one of SEQ ID NOs: 1-10, preferably to SEQ ID NO: 1, SEQ ID NO: 2, or SEQ ID NO: 3. Each individual bacteriophage may be one that is not prone to generalized transduction and/or does not carry antibiotic resistance genes. The phage can be naturally occurring or non-naturally occurring. In some embodiments for example, in compositions with more than one bacteriophage, at least one can be naturally occurring, at least one can be non-naturally occurring, or none can be naturally occurring. The compositions optionally may include a cryoprotectant or excipient. The excipient may stabilize phage potency or reduce potency loss over time, for example.

In some embodiments, bacteriophage compositions provided herein further include a pharmaceutically acceptable carrier, diluent, excipient or combinations thereof. Suitable carriers, diluents and/or excipients may include isotonic saline solutions, such as phosphate-buffered saline. "Pharmaceutically acceptable excipient" and "pharmaceutically acceptable carrier" refer to a substance that aids the administration of an active agent to and/or absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts e.g. for influencing osmotic pressure, buffers, coloring, and/or aromatic substances and the like that do not deleteriously react with the compounds of the disclosure. One of skill in the art will recognize that other pharmaceutical excipients are useful in the present disclosure.

A bacteriophage composition as described herein may be formulated as a disinfectant composition. The disinfectant composition may be in the form of a spray or liquid wash for a surface. The composition may be a hand wash. Suitably where the composition is a formulation for topical application, it may take the form of a lotion, cream, ointment, paste, gel, foam, or any other physical form as a carrier generally known for topical administration. Such thickened topical formulations are particularly advantageous because the formulations adhere to the area of the skin on which the material is placed, thus allowing a localized high concentration of bacteriophages to be introduced to the particular area to be disinfected. For example, paraffin- and lanolin-based creams, which are particularly useful for the application of product to the nasal cavity, are generally known in the art. However, other thickeners, such as polymer thickeners, may be used. The formulations may also comprise one or more of the following: water, preservatives, active surfactants, emulsifiers, anti-oxidants, or solvents.

A bacteriophage composition as described herein may be formulated for nasal, oral, parenteral, intramuscular, intra-articular, intravenous, subcutaneous, transdermal, ocular or aural administration. Such a bacteriophage preparation may be used directly, refrigerated, lyophilized, stored frozen in aqueous or other solution, optionally with an appropriate cryoprotectant (e.g. 20% glycerol), freeze dried and rehydrated prior to use, or rendered stable in some other formulation including (but not limited to) tablet, emulsion, ointment, or impregnated wound dressing or other item. In embodiments, the cryoprotectant is 10-30% glycerol. In embodiments, the cryoprotectant is 10%, 11%, 12%, 13%, 14%, 15%, 16%, 17%, 18%, 19% 20%, 21%, 22%, 23%, 24%, 25%, 26%, 27%, 28%, 29%, or 30% glycerol. In embodiments, the bacteriophage composition includes saline (e.g., phosphate buffered saline, with or without magnesium). In embodiments, the bacteriophage composition includes a buffer. In embodiments, the buffer includes calcium or magnesium salts. In an embodiment, the buffer includes phosphate buffered saline and $MgSO_4$. The buffer may include 1 mM to 20 mM $MgSO_4$, 2 mM to 19 mM $MgSO_4$, 3 mM to 17 mM $MgSO_4$, 4 mM to 16 mM $MgSO_4$, 5 mM to 15 mM $MgSO_4$, 6 mM to 14 mM $MgSO_4$, 7 mM to 13 mM $MgSO_4$, 8 mM to 12 mM $MgSO_4$, 9 mM to 11 mM $MgSO_4$, or about 10 mM $MgSO_4$. The concentration may be any value or subrange within the recited ranges, including endpoints. For example, the buffer may include about 1 mM $MgSO_4$, about 2 mM $MgSO_4$, about 3 mM $MgSO_4$, about 4 mM $MgSO_4$, about 5 mM $MgSO_4$, about 6 mM $MgSO_4$, about 7 mM $MgSO_4$, about 8 mM $MgSO_4$, about 9 mM $MgSO_4$, about 10 mM $MgSO_4$, about 11 mM $MgSO_4$, about 12 mM $MgSO_4$, about 13 mM $MgSO_4$, about 14 mM $MgSO_4$, about 15 mM $MgSO_4$, about 16 mM $MgSO_4$, about 17 mM $MgSO_4$, about 18 mM $MgSO_4$, about 19 mM $MgSO_4$, or about 20 mM $MgSO_4$.

A bacteriophage composition may be formulated for nasal, oral, parenteral, intra-articular, intramuscular, intravenous, subcutaneous, transdermal, ocular or aural administration. Such a bacteriophage preparation may be used directly, stored frozen in aqueous or other solution, optionally with an appropriate cryoprotectant (e.g., 10% sucrose or glycerol), stored in refrigeration temperatures, freeze dried and rehydrated prior to use, or rendered stable in some other formulation including (but not limited to) tablet, emulsion, ointment, or impregnated wound dressing or other item. In some embodiments, the bacteriophage composition may be comprised in an intravenous delivery means.

In some embodiments, the bacteriophage composition is sterile. Such a sterile product may be suitable for parenteral administration in a subject.

In some embodiments, provided herein are aerosol formulations including the bacteriophage and/or bacteriophage compositions/formulations as described herein. Some embodiments relate to methods and uses of such aerosol formulations.

In embodiments, a bacteriophage composition described herein is formulated for intravenous (IV) administration. Intravenous administration may be by intravenous push or using an IV bag.

Uses/Methods of Use

Provided herein is a use of one or more bacteriophage or a bacteriophage composition as a medicament (e.g., for treating a *Staphylococcus* infection). Corresponding methods of treating a disease comprising administration of the one or more bacteriophage or bacteriophage composition(s) to a subject are also provided. In some embodiments the treatment of illnesses/diseases as set forth in U.S. Patent Publication No. 2017-0065649 and WO 2018/146437 (incorporated herein by reference in its entirety for all of its bacteriophage, compositions, components, excipients and methods) is specifically excluded from the methods described herein. For example, in some embodiments, methods of treating pulmonary infections can be specifically excluded.

In an aspect, there is provided a bacteriophage composition for use in treating a bacterial infection. In related aspects, there is provided use of a bacteriophage composition in the manufacture of a medicament for treating a bacterial infection, as well as a method of treating a bacterial infection comprising administering the bacteriophage composition to a subject.

In an aspect, provided herein are methods of treating a bacterial infection including selecting a subject with a confirmed *Staphylococcus* infection and administering a bacteriophage composition as described herein. In one embodiment, the method comprises selecting a subject with a *Staphylococcus* infection that has not responded to treatment with one or more antibiotics.

The bacteriophage compositions are useful in treating a *Staphylococcus* (e.g. *S. aureus*) bacterial infection. In one embodiment, the bacterial infection is a sinus, nasal or respiratory infection. In one embodiment, the bacterial infection is rhinosinusitis. In one embodiment, the bacterial infection is a urinary tract infection (or complicated urinary tract infection), intra-abdominal infection (or complicated intra-abdominal infection), septicemia (e.g., septicemia due to burns, uncontrolled bacteremia), or bacteremia (e.g., due to pneumonia, urinary tract infection, endocarditis, etc). In one embodiment, the bacterial infection is an implant infection, such as a cardiac implant infection (e.g., ventricular assist device infection; pacemaker infection) or prosthetic joint infection. In one embodiment, the bacterial infection is endocarditis or prosthetic valve endocarditis. In one embodiment, the bacterial infection is a skin infection or skin structure infection. In a preferred embodiment, the bacterial infection is not a pulmonary infection. In one embodiment, the bacterial infection is a hospital or nosocomial infection.

In some embodiments, the infection is characterized by the presence of a bacterial biofilm.

In some embodiments, the subject has a bacterial infection that is not responding to one or more antibiotics. In some embodiments, the subject has a bacterial infection that is not responding to standard-of-care antibiotics.

In embodiments, one or more bacterial isolates from the subject is tested for susceptibility to the bacterial composition prior to administration.

A use or method as described herein typically comprises administering a bacteriophage composition described herein to a subject. As used herein, a "subject" is a mammal, such as a human or other animal. Preferably, the term "subject" refers to a human subject. In one embodiment, the subject is a human subject with a *Staphylococcus* infection (e.g. a *S. aureus* infection).

A bacteriophage composition may be administered to a subject in a therapeutically effective amount or a prophylactically effective amount.

As used herein, a "therapeutically effective amount" is any amount of the composition, which when administered alone or in combination to a subject for treating a bacterial infection (or a symptom thereof) is sufficient to effect such treatment of the infection, or symptom thereof.

As used herein, a "prophylactically effective amount" is any amount of the composition that, when administered alone or in combination to a subject inhibits or delays the onset or reoccurrence of a bacterial infection (or a symptom thereof). In some embodiments, the prophylactically effective amount prevents the onset or reoccurrence of a bacterial infection entirely. "Inhibiting" the onset means either lessening the likelihood of a bacterial infection's onset (or symptom thereof), or preventing the onset entirely.

An appropriate dosage range is one that produces the desired therapeutic effect (e.g., the composition is dosed in a therapeutically or prophylactically effective amount).

In one embodiment, the subject is a human subject with a *Staphylococcus* infection (e.g., a *Staphylococcus aureus* infection). In embodiments, the composition includes $1\times10^5$ to $1\times10^{11}$ PFU of each phage per ml of composition. In embodiments, the composition includes $1\times10^5$ to $1\times10^6$ PFU, $1\times10^5$ to $1\times10^7$ PFU, $1\times10^5$ to $1\times10^8$ PFU, $1\times10^5$ to $1\times10^9$ PFU, or $1\times10^5$ to $1\times10^{10}$ PFU of each phage per ml of composition. In embodiments, the composition includes $1\times10^6$ to $1\times10^7$ PFU, $1\times10^6$ to $1\times10^8$ PFU, $1\times10^6$ to $1\times10^9$ PFU, $1\times10^6$ to $1\times10^{10}$ PFU, or $1\times10^6$ to $1\times10^{11}$ PFU of each phage per ml of composition. In embodiments, the composition includes $1\times10^7$ to $1\times10^8$ PFU, $1\times10^7$ to $1\times10^9$ PFU, $1\times10^7$ to $1\times10^{10}$ PFU, or $1\times10^7$ to $1\times10^{11}$ PFU of each phage per ml of composition. In embodiments, the composition includes $1\times10^8$ to $1\times10^9$ PFU, $1\times10^8$ to $1\times10^{10}$ PFU, or $1\times10^8$ to $1\times10^{11}$ PFU of each phage per ml of composition. In embodiments, the composition includes $1\times10^9$ to $1\times10^{10}$ PFU or $1\times10^9$ to $1\times10^{11}$ PFU of each phage per ml of composition. In embodiments, the composition may include $1\times10$ PFU to $1\times10^{11}$ PFU of each phage per ml of composition. In embodiments, a bacteriophage composition is administered to a subject at a dosage of at least about $1\times10^5$ PFU of each phage, at least about $1\times10^6$ PFU of each phage, at least about $1\times10^7$ PFU of each phage, at least about $1\times10^8$ PFU of each phage, at least about $1\times10^9$ PFU of each phage, at least about $1\times10^{10}$ PFU of each phage, or at least about $1\times10^{11}$ PFU of each phage per ml of composition. In embodiments, one or more bacteriophage(s) may be combined to form a composition include $1\times10^5$, $1\times10^6$, $1\times10^7$, $1\times10^8$, $1\times10^9$ or $1\times10^{10}$, or $1\times10^{11}$ PFU of each phage per ml of composition. Dosages include any value or range within the recited ranges, including endpoints.

In some embodiments, bacteriophage compositions provided herein are administered to a subject at a dosage of at least about $1\times10^5$ PFU total phage, at least about $1\times10^6$ PFU total phage, at least about $1\times10^7$ PFU total phage, at least about $1\times10^8$ PFU total phage, at least about $1\times10^9$ PFU total phage, at least about $1\times10^{10}$ PFU total phage, or at least about $1\times10^{11}$ PFU of total phage. The bacteriophage composition is administered at a dosage of between about $1\times10^5$ to about $1\times10^{11}$ PFU of total phage per ml of composition. In embodiments, the bacteriophage composition is administered at a dosage of between about $1\times10^5$ to about $1\times10^6$ PFU, between about $1\times10^5$ to about $1\times10^7$ PFU, between about $1\times10^5$ to about $1\times10^8$ PFU, between about $1\times10^5$ to about $1\times10^9$ PFU, or between about $1\times10^5$ to about $1\times10^{10}$ PFU of total phage per ml of composition. In embodiments, the bacteriophage composition is administered at a dosage of between about $1\times10^6$ to about $1\times10^7$ PFU, between about $1\times10^6$ to about $1\times10^8$ PFU, between about $1\times10^6$ to about $1\times10^9$ PFU, between about $1\times10^6$ to about $1\times10^{10}$ PFU, or between about $1\times10^6$ to about $1\times10^{11}$ PFU of total phage per ml of composition. In embodiments, the bacteriophage composition is administered at a dosage of between about $1\times10^7$ to about $1\times10^8$ PFU, between about $1\times10^7$ to about $1\times10^9$ PFU, between about $1\times10^7$ to about $1\times10^{10}$ PFU, or between about $1\times10^7$ to about $1\times10^{11}$ PFU of each phage per ml of composition. In embodiments, the bacteriophage composition is administered at a dosage of between about $1\times10^8$ to about $1\times10^9$ PFU, between about $1\times10^8$ to about $1\times10^{10}$ PFU, or between about $1\times10^8$ to about $1\times10^{11}$ PFU of total phage per ml of composition. In embodiments, the bacteriophage composition is administered at a dosage of between about between about $1\times10^9$ to about $1\times10^{10}$ PFU, or between about $1\times10^9$ to about $1\times10^{11}$ PFU of total phage per ml of composition. In embodiments, the bacteriophage composition is administered at a dosage of between about $1\times10^{10}$ to about $1\times10^{11}$ PFU of total phage per ml of composition. A dosage may be $3\times10^9$ PFU per milliter composition. Dosages include any value or range within the recited ranges, including endpoints.

In some embodiments, the bacteriophage composition is administered at least once, twice, three times, or four times daily. Suitably the bacteriophage composition may be administered twice daily. In one embodiment, therefore, a dosage of at least about $1\times10^5$ PFU of each phage is administered at least once, twice, three times, or four times daily. In one embodiment, therefore, a dosage of at least about $1\times10^6$ PFU of each phage is administered at least once, twice, three times, or four times daily. In another embodiment at least about $1\times10^7$ PFU of each phage is administered at least once, twice, three times, or four times daily. In a further embodiment at least about $1\times10^8$ PFU of each phage is administered at least once, twice, three times, or four times daily. In another embodiment at least about $1\times10^9$ PFU of each phage is administered at least once, twice, three times, or four times daily. In another embodiment at least about $1\times10^{10}$ PFU of each phage is administered at least once, twice, three times, or four times daily. In another embodiment at least about $1\times10^{11}$ PFU of each phage is administered at least once, twice, three times, or four times daily. A dosage range between about $1\times10^5$ PFU of each phage to about $1\times10^{11}$ PFU of each phage may be administered at least once, twice, three times, or four times daily. Preferably a dosage range between about $1\times10^7$ PFU of each phage to about $1\times10^9$ PFU of each phage may be administered at least once, twice, three times, or four times daily.

In some embodiments, the bacteriophage composition is administered every 2 hours, every 4 hours, every 6 hours, every 8 hours, every 12 hours, every 24 hours, every 48 hours, or every 72 hours. In some embodiments, the bacteriophage composition is administered every 2 hours. In some embodiments, the bacteriophage composition is administered every 4 hours. In some embodiments, the bacteriophage composition is administered every 6 hours. In some embodiments, the bacteriophage composition is administered every 8 hours. In some embodiments, the bacteriophage composition is administered every 12 hours. In some embodiments, the bacteriophage composition is administered every 24 hours. In some embodiments, the bacteriophage composition is administered every 48 hours. In some embodiments, the bacteriophage composition is administered every 72 hours. Frequency of administration include any value or range within the recited ranges, including endpoints.

In some embodiments, the bacteriophage composition is administered for at least one day, at least 2 days, at least 3 days, at least 4 days, at least 5 days, at least 6 days, one week, at least two weeks, at least three weeks, at least four weeks, at least 5 weeks, at least 6 weeks, at least 7 weeks, at least 8 weeks, at least 9 weeks, at least 10 weeks, or more than 10 weeks. In some embodiments, the bacteriophage composition is administered for at least one day. In some embodiments, the bacteriophage composition is administered for at least one week. In some embodiments, the bacteriophage composition is administered for at least two weeks. In some embodiments, the bacteriophage composition is administered for at least three weeks. In some embodiments, the bacteriophage composition is administered for at least four weeks. In some embodiments, the bacteriophage composition is administered for at least five weeks. In some embodiments, the bacteriophage composition is administered for at least six weeks. In some embodiments, the bacteriophage composition is administered for between about 3 days and about 100 days. In an embodiment, the bacteriophage composition is administered for between about 7 days and about 60 days. In an embodiment, the bacteriophage composition is administered for between about 14 days and about 30 days. In an embodiment, the bacteriophage composition is administered for between about 3 days and about 28 days. In an embodiment, the bacteriophage composition is administered for at least 14 days. In an embodiment, the bacteriophage composition is administered for greater than 14 days. Duration of administration includes any value or range within the recited ranges, including endpoints.

A bacteriophage composition for use as a medicament may be administered by any route selected on the basis of the condition to be treated. In one embodiment the route of administration is nasal, oral, pulmonary, parenteral, intramuscular, intra-articular, intravenous, subcutaneous, transdermal, ocular, aural or combinations thereof. When used in the treatment of a pulmonary bacterial infection, the bacteriophage composition may be administered nasally or orally, for example via aerosolisation or nebulization using an appropriate pulmonary delivery means, such as an inhaler, nebulizer, or respirator. The composition may be administered to the patient via more than one route, for example intravenously and by inhalation, or intravenously and intra-articularly.

In one embodiment an antibiotic (suitably a chemical antibiotic) may be administered in combination with the bacteriophage composition. Combinatorial administration of antibiotics and bacteriophages is taught in WO 2008/110840 and WO 2005/009451, which teaching is incorporated herein by reference in its entirety for all of its compositions, bacteriophage, components/excipients and methods. The antibiotic may be administered simultaneously or sequentially with the bacteriophage composition. Suitably, the one or more antibiotics may be administered after the composition such that bacteriophage replication has become established before antibiotic treatment begins. In this case, antibiotic treatment may be delayed for one or more hours or days from application of the one or more bacteriophages, e.g., from 1 to 2, 3, 4, 5, 6, 7, 8, 9 or 10 days. Where a bacteriophage composition comprising a plurality of bacteriophages is employed with each member of the composition exhibiting different strain specificity, it will suffice that at least a proportion (e.g., one or more bacteriophage(s)) of the composition is capable of targeting the bacterial infection.

Thus, in some embodiments a bacteriophage composition comprises one or more antibiotics, such as one or more chemical antibiotics. An antibiotic may be selected based on sensitivity of a *Staphylococcus* species or strain to said antibiotic. The antibiotic(s) include antibiotics selected from a class of antibiotics including fluoroquinolone, carbapenem, aminoglycoside, ansamycin, cephalosporin, penicillin, beta lactam, beta lactamase inhibitor, folate pathway inhibitor, fucidane, glycopeptide, glycylcycline, lincosamide, lipopeptide, macrolide, oxazolidinone, phenicol phosphonic acid, streptogramin, or tetracycline. In some embodiments, one or more of the above antibiotics can be specifically excluded from the compositions and methods herein. In some embodiments, the antibiotic can be used as a co-treatment that is not part of the same composition. Suitably the *Staphylococcus* species or strain may be the same species or strain present in a subject to be treated. In one embodiment a *Staphylococcus* species or strain is taken from a subject to be treated and tested for antibiotic sensitivity. Sensitivity may be determined by in vitro sensitivity assays known in the art.

Alternatively or additionally, an antibiotic may be selected because it is known to be active against a bacteria known to be (or thought likely to be) present together with a *Staphylococcus* infection to be treated (e.g., as part of a bacterial biofilm).

In one embodiment an antibiotic is one or more selected from: vancomycin, teicoplanin, penicillin, methicillin, flucloxacillin, dicloxacillin, cephalosporins (e.g., cefazolin, cephalothin, cephalexin), clindamycin, lincomycin, erythromycin, or combinations thereof. Suitably the antibiotic may be vancomycin and/or teicoplanin. In some embodiments, one or more of the above antibiotics can be specifically excluded from the compositions and methods herein.

Provided herein are uses or methods including administration of a bacteriophage composition to a subject in vivo; in vitro monitoring of the sensitivity of a sample of bacterial cells from an infection (e.g. present in the subject) or from another infection by the same strain to one or more antibiotic(s); and administration of said one or more antibiotic(s), when it has been established that said sensitivity to said one or more antibiotic(s) has been induced.

In an embodiment, provided herein is a method for restoring sensitivity to an antibiotic(s) by administering a composition as described herein. In embodiments. provided is a method for disrupting a biofilm by administering a composition as described herein. In an embodiment is provided a method for destroying a biofilm by administering a composition as described herein.

In an embodiment, the antibiotic (e.g. chemical antibiotic) is administered at a time period at which sensitivity of sampled bacteria to the antibiotic is induced by the composition. In some embodiments, the time period may be 6 hours, 12 hours, 24 hours, or 48 hours. In other embodiments, the bacteriophage composition and the antibiotic may be administered at intervals of one day to two months apart, preferably at intervals of one to four weeks apart, suitably at intervals of two weeks apart.

In one embodiment is provided a method for restoring sensitivity to an antibiotic(s) by administering a composition as described herein. In one embodiment is provided a method for disrupting a biofilm by administering a composition as described herein. In one embodiment is provided a method for destroying a biofilm by administering a composition as described herein.

In one embodiment a bacteriophage composition may be used in a method of killing *Staphylococcus* (e.g., *S. aureus*) bacteria on a surface, said method comprising applying a bacteriophage composition (e.g., formulated as a disinfectant composition) to the surface. Suitably, the surface is a site of contamination or prospective site of contamination.

In one embodiment, the surface is the skin of a mammal (e.g., a human). Alternatively or additionally, the surface may be equipment (suitably medical equipment), bedding, furniture, walls or floors (e.g., in a clinical environment).

Some aspects relate to, for example, a kit comprising: a bacteriophage composition; and instructions for use of same (e.g., in medicine). The kit may further comprise an antibiotic (e.g., a chemical antibiotic) and optionally instructions for use of same in combination with the bacteriophage composition.

In one embodiment, the instructions provide details for dosing a bacteriophage composition as described herein. In one embodiment, the instructions included in a kit are for use of in treating a *Staphylococcus* infection.

Some aspects relate to, for example, use of a bacteriophage composition or kit for non-medical applications. For example, a bacteriophage composition or kit may be used in food hygiene, agriculture or crop protection, and/or in environmental hygiene applications. Thus, in one embodiment the kit comprises instructions for use of a bacteriophage composition in a non-medical application.

A bacteriophage composition may also be comprised in a bandage or wound dressing. The wound dressing may be a pad or sticking plaster-type dressing. The bacteriophages may be applied to the wound dressing or bandage as a disinfectant formulation or topical cream, prior to applying to the wound dressing or bandage. Alternatively, the wound dressing or bandage may be soaked in a carrier containing the bacteriophages and dried to impregnate said bacteriophages within the dressing or bandage. Bacteriophages may also be adsorbed onto the surface of the bandage or wound dressing using techniques generally known in the art. The advantage of this approach is that the bandage or wound dressing allows the bacteriophages to be brought into contact with a wound, which may contain the bacteria. One aspect relates to, for example, methods of inhibiting or treating bacteria by applying a bandage or wound dressing to a subject.

The bacteriophage composition is particularly advantageous for use in medicine, and shows clinical efficacy in the treatment of *Staphylococcus* infections.

Additionally, the bacteriophage composition is efficacious against a broad spectrum of *Staphylococcus* species and strains.

A combination of a bacteriophage composition and an antibiotic (e.g., a chemical antibiotic) may provide an enhanced (e.g., synergistic) therapeutic over the antibiotic therapy alone.

Unless defined otherwise, all technical and scientific terms used herein have the same meaning as commonly understood by one of ordinary skill in the art to which this disclosure belongs.

This disclosure is not limited by the example methods and materials disclosed herein, and any methods and materials similar or equivalent to those described herein can be used in the practice or testing of embodiments of this disclosure. Numeric ranges are inclusive of the numbers defining the range. The headings provided herein are not limitations of the various aspects or embodiments of this disclosure which can be had by reference to the specification as a whole. Accordingly, the terms defined immediately below are more fully defined by reference to the specification as a whole.

Other definitions of terms may appear throughout the specification. Before the example embodiments are described in more detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

The publications discussed herein are provided solely for their disclosure prior to the filing date of the present application. Nothing herein is to be construed as an admission that such publications constitute prior art to the claims appended hereto. All publications referenced herein are incorporated herein by reference in their entireties for all of their teachings, including, but not limited to, all bacteriophage, compositions, components, excipients, and methods.

EXAMPLES

Example 1: Assembly of a 3 Phage Bacteriophage Composition

Experiments were conducted to create a bacteriophage therapy that met the following criteria: 1) Obligately lytic, to avoid specialized transduction of bacterial genes; 2) Not known, by empirical testing and/or inference from genomics, to be prone to generalized transduction, and 3) Fully sequenced, to avoid phages with genes known to carry antibiotic resistance or bacterial virulence genes, and to help assess other lifestyle traits.

Collectively, the phages used together to treat a patient should: 1) Have broad activity against the target pathogen but not other species, to maximize potential utility and minimize off-target effects, and 2) Be capable of complementation, in which resistant mutants arising to one phage are sensitive to another phage.

In addition to characteristics of the phages themselves, material for clinical use should be produced in such a way as to give confidence that the final product retains these characteristics (i.e. are still the same phages) and does not contain potentially harmful (or harmful amounts) of impurities such as endotoxin or host cell proteins.

Each of the selected phages was isolated from an environmental source and subsequently paired to a well-characterized S. aureus strain that serves as its manufacturing host. After passaging and iterative selection, candidate phages were selected. The genomic sequences of these are not the same as the original, naturally-occurring sequence. Host-paired phages were purified to ensure that the resulting master stocks produced genetically and phenotypically consistent batches of each phage. Unless otherwise stated, all data is derived from the host-paired, plaque-purified phages. Phages were propagated in liquid culture using vegetable peptone media (VP0101, Oxoid, UK). Lysates were passed through a 0.2 µm filter to remove large cellular debris and, depending on the needs of subsequent testing, optionally subjected to a proprietary process of column-based purification steps to further remove host cell proteins and other bacterial debris and to replace growth medium with phosphate-buffered saline (PBS) containing 10 mM magnesium sulfate (PBS+Mg). Equal concentrations of each bacteriophage were combined to form the bacteriophage cocktail (known as AB-SA01). The bacteriophage are genetically consistent throughout storage and production processes.

Bacteria: AB-SA01 manufacturing hosts are S. aureus strains originally isolated from humans. The S. aureus diversity panel and the species-specificity panel were sourced from the American Type Culture Collection (Manassas, USA), the Walter Reed Army Institute of Research Multidrug-resistant Organism Repository and Surveillance Network ("MRSN", Silver Spring, USA), and clinical sites in Australia and the UK. Global surveillance panels of S. aureus strains were obtained from JMI Laboratories (North Liberty, USA). Targeted interest panels include chronic rhinosinusitis (CRS) strains from Belgium, and vancomycin intermediate (VISA) strains from the Centers for Disease Control (CDC) and Food and Drug Administration (FDA) Antimicrobial Resistance Isolate Bank (Atlanta, USA). The definitions of multidrug resistant (MDR) and extensively drug resistant (XDR) strains are according to Magiorakos et al (Clin Microbiol Infect 18(3): 268-281, 2012).

Phage sensitivity assays: Testing on the S. aureus panels used Heart Infusion Broth, amended with 1.5% agar for plates or 0.7% agar for overlays. Phage activity was assessed using a modification of the small drop agar overlay method (Mazzocco et al, Methods Mol Biol. 2009; 501:81-5, 2009). Briefly, 100 µL of 16-18 h planktonic bacterial culture was mixed with molten 0.7% top agar and poured evenly over an agar plate. When the top agar layer was set, serial dilutions of standardized phage solutions were spotted onto the overlay and plates incubated overnight at 37° C. Phage activity was indicated by clearing of the bacterial lawn at the site of phage application, and by the development of individual plaques as the phage sample is diluted. Strains were only considered sensitive if discrete plaques could be observed as the sample was diluted, indicating phage replication. Testing on the species-specificity panel was conducted similarly, using media recommended for the specific bacterial species and bacterial culture volumes suitable to produce a uniform lawn.

Frequency of resistance and complementation: Complementation studies conducted during product selection used apparent bacteriophage insensitive mutant (BIM) colonies that were isolated after infecting a sensitive S. aureus strain with individual candidate phages. Colonies were streak-purified on agar plates. To screen for phage sensitivity, 10 µL spots of PBS or phage (~1×10$^9$ PFU/mL; PFU: plaque forming units) were spotted onto Nutrient Agar plates. After 10 min, 5 µL of overnight Nutrient Broth culture from each BIM or the parental strain was applied to each phage spot. After 24 h incubation at 37° C., phage+bacteria spots were compared to PBS+bacteria controls and scored as R (resistant; no difference from control spot), I (intermediate, phage activity seen within bacterial spot), or S (sensitive, <10 bacterial colonies in spot). For the final AB-SA01 composition, the frequency of spontaneous phage resistance in triplicate populations of the same S. aureus strain was assessed using a modification of O'Flynn et al (2004 Appl Environ. Microbio. 70(6):3417-3424). In 200 µL, 6-8×10$^8$ CFU (colony forming units) was mixed with 2-3×10$^9$ PFU of purified phage (AB-SA01 or individual components), incubated for 10 min at 37° C., then mixed with 3 mL molten 0.4% Nutrient Agar and poured over a 10 mm round 1.5% Nutrient Agar plate. Bacterial colonies were counted after 24 h and 48 h incubation at 37° C. The apparent frequency of BIMs was calculated as the number of colonies on each test plate divided by the input number of bacteria in that replicate. Results were compared using a repeated measures ANOVA and a priori planned comparisons between AB-SA01 and the 3 component phages were conducted using paired t-tests. Up to 10 BIMs from each phage+host combination (all BIMs if <10) were streak-purified on agar plates and tested for the presence of heritable resistance using the spot dilution method of phage sensitivity testing.

Genome sequencing and analysis: Phage genomic DNA was purified from filtered lysates or purified preparations and sequenced by Illumina paired-end (ACGT) or PacBio technologies (Expression Analysis), using FOR-free libraries. Annotation was conducted using myRAST. Similarities of annotated proteins to integrases and annotated genes to bacterial virulence or antibiotic resistance genes were assessed using blast searches requiring at least 30% identity across 50% of the sequence, and E≤0.05, any hits were manually inspected for validity based on factors such as the likely accuracy of the hit's original annotation and evidence from secondary structure predicted by HHPred (Soding et al. 2005, Bioinformatics. 21(7):951-960; Soding et al. 2005, Nucl. Acid Res. 33(suppl 2):W244-W248, 2005). Genome alignments were constructed using Progressive Mauve with the default parameters (Darling et al. 2004, Genome Res 14(7):1394-1403).

Animal studies: Purified phage material was used for all animal studies. AB-SA01: Three groups of five female BALB/c mice were anesthetized and an inoculum of $3.0 \times 10^8$ CFU of methicillin-sensitive S. aureus strain Xen29 (Perkin Elmer) was delivered intranasally (IN) in a volume of 35 µL. At 2 and 6 hours post infection (hpi), untreated controls received 50 µL PBS—Mg IN and the phage treatment group received $5 \times 10^8$ PFU per phage in a 50 µL IN dose. At 2, 6, and 12 hpi, the antibiotic controls received 110 mg/kg vancomycin as a SC injection. At 24 hpi, mice were euthanized by $CO_2$ inhalation and lungs processed for bacterial titers. Bacterial counts were enumerated on Mueller Hinton agar and the treatment groups compared to the control using ANOVA on $log_{10}$-transformed values with Dunnett's test multiple comparisons to control. After both mouse studies, bacteria recovered from mouse lung tissue were tested for phage sensitivity as previously described.

Physicochemical characteristics of AB-SA01 component phages: All three AB-SA01 component phages produce small, clear plaques when plated on their paired S. aureus hosts. Transmission electron microscopy (TEM) images of the three AB-SA01 component phages show the straight, contractile tail and narrow neck that are characteristic of phages belonging to the order Caudovirales, family Myoviridae (FIG. 1).

Figure 2:
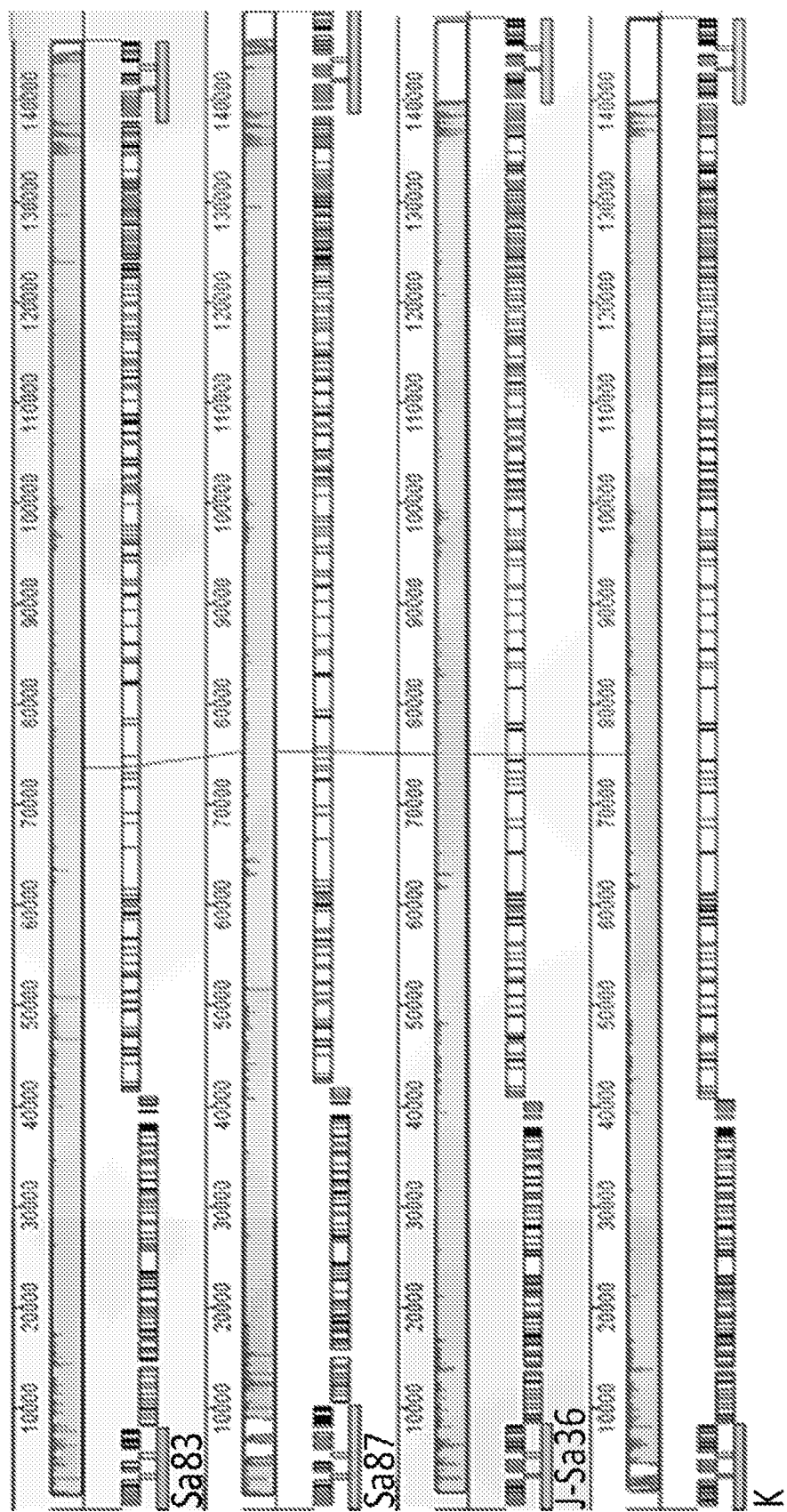
FIG. 2 shows a Progressive Mauve alignment of (top to bottom) Sa83, Sa87, J-Sa36, and phage K (GenBank Accession No. K766114), each showing annotated genes (white boxes) and long terminal repeats (red boxes). Interruptions in the red blocks above each annotated genome indicate differences in nucleotide sequences.
Figure 3B:
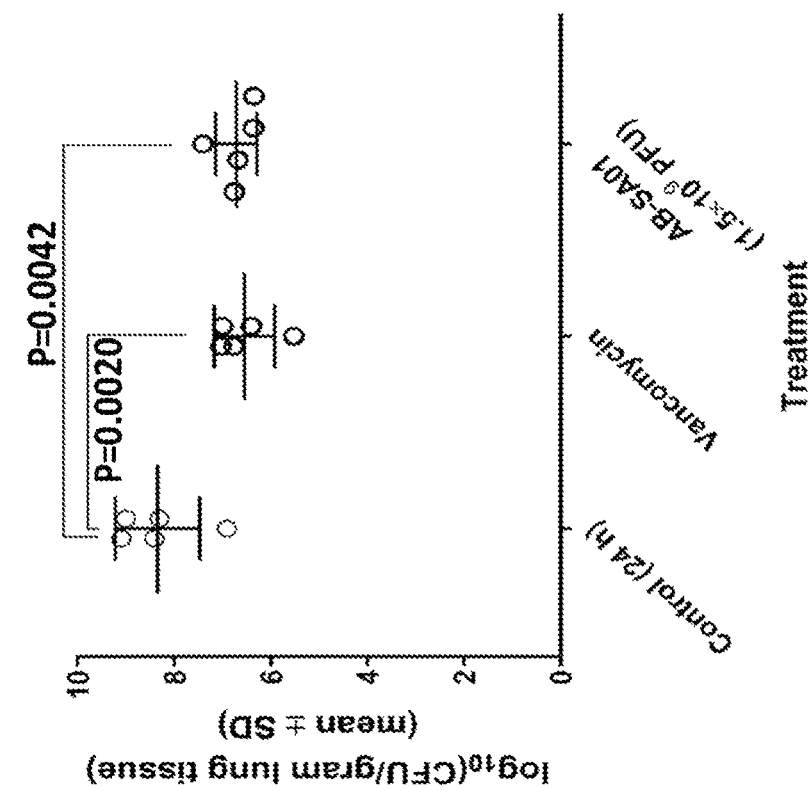
FIGS. 3A and 3B are graphs showing a composition of phage according to one or more aspects described herein (AB-SA01) reduces lung bacterial burden in neutropenic CD-1 mice (2A) and immunocompetent BALB/c mice (2B). Phage doses are given as total PFU per dose.
Figure 3A:
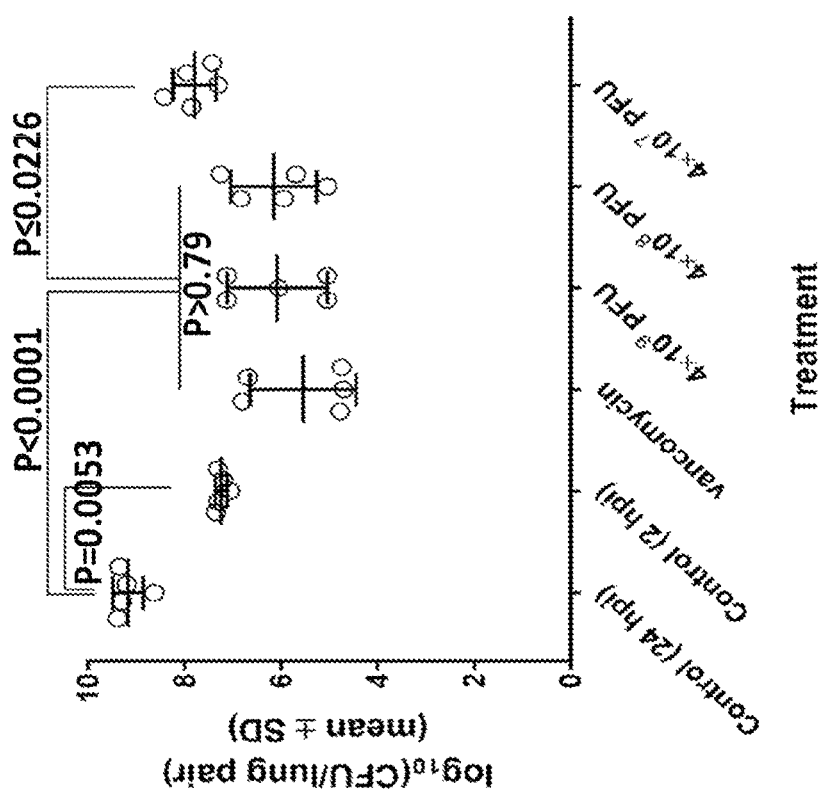

All AB-SA01 component phages were sequenced from amplification-free libraries capable of revealing the relative frequencies of genome regions. Read-mapping data showed regions of approximately doubled coverage identifying the genome termini and associated fixed direct terminal repeats between approximately 8 and 10 kb. This genome structure indicates a sequence-specific packaging mechanism not associated with generalized transduction. The pairwise relatedness of the collinear single-copy component phage genomes ranges from 93 to 97% nucleotide identity (FIG. 2) and all are related to well-studied S. aureus myovirus phage K. No identifiable integrases were found in the AB-SA01 component phage genomes and none of the ca. 200 predicted phage genes in each of the three phages were similar to known bacterial virulence or antibiotic resistance genes.

In Vitro Activity of AB-SA01

The target species for AB-SA01 is S. aureus. Overall, 94% of 401 clinical S. aureus isolates were sensitive to AB-SA01 (Table 1), including 95% of the 205 isolates known to be MDR, and with little apparent variation by genetic lineage, year of isolation, or infection type. When tested on representatives of normal human microflora and related staphylococci, AB-SA01 and its component phages showed some activity against two of five tested S. epidermidis strains, but no cross-genus activity (Table 2). When tested on S. aureus strains, no evidence of interference among the component phages was observed. The titers observed for AB-SA01 were mostly consistent with the component phage activities, with a few cases of possible synergy in which AB-SA01 generated plaques even though none of the component phages did. In addition, bacteriophage that have less than 10% nucleic acid variation across the entire genome when compared to any one of Sa87, J-Sa36, or Sa83 were tested against seven S. aureus isolates. Representative data for two phage is shown in Table 3.

The AB-SA01 component phages were selected partly based on the 68-member diversity panel, which includes representatives of all major community-acquired (CA-) and hospital-acquired (HA-) MRSA lineages (Stefani et al. 2012, Int J Antimicrob Agents 39(4): 273-282; Otter et al. 2010, Lancet Infect Dis 10(4): 227-239). Each component phage had a different host range, with most bacterial strains being sensitive to more than one of the AB-SA01 phages. AB-SA01 activity was similarly high across panels of isolates that represent globally prevalent S. aureus from blood, wound, lung, urinary and other infections in later years. Using targeted interest panels, AB-SA01 was also shown to have activity on strains having the relatively rare but concerning VISA phenotype, a panel of exclusively CRS isolates, and a variety of the clinically significant USA300 lineage.

TABLE 1

Phage activity against S. aureus

| Panel Type | Phage Panel | Percentage of Isolates Sensitive to Indicated Phage | | | |
|---|---|---|---|---|---|
| | | Sa83 | Sa87 | J-Sa36 | AB-SA01 |
| Selection | AmpliPhi Reference Panel (n = 68) [1] | 85.2% | 86.8% | 76.4% | 94.1% |
| Prevalence [2] | 2013 Global Panel (n = 53) | 96.2% | 96.2% | 86.8% | 100% |
| | 2015 Global Panel (n = 60) | 85.0% | 93.3% | 75.0% | 93.3% |
| | 2016 Global Panel (n = 60) | 80.0% | 83.3% | 63.3% | 88.3% |
| Targeted | CDC VISA Panel (n = 14) | 64.3% | 64.3% | 64.3% | 64.3% |
| | Regional USA300 Panel (n = 29) [3] | 100% | 100% | 100% | 100% |
| | Ghent CRS Panel (n = 90) | NT | NT | NT | 96.7% |

TABLE 1-continued

Phage activity against *S. aureus*

| Panel Type | Phage Panel | Percentage of Isolates Sensitive to Indicated Phage | | | |
|---|---|---|---|---|---|
| | | Sa83 | Sa87 | J-Sa36 | AB-SA01 |
| NA | Expanded Access Requests (n = 27) [4] | 85.2% | 92.6% | 88.9% | 96.3% |
| | Summary Values | Diversity Panels: Selection & Prevalence (n = 241) | | | 93.8% |
| | | All Panels (n = 401) | | | 94.0% |

TABLE 2

In vitro activity of AB-SA01 and its component phages on bacterial species other than *S. aureus*

| Bacteria | No. Strains Tested | No. Strains Productively Infected | | | |
|---|---|---|---|---|---|
| | | Sa83 | Sa87 | J-Sa36 | AB-SA01 |
| *Achromobacter xylosoxidans* | 1 | 0 | 0 | 0 | 0 |
| *Acinetobacter baumanii* | 1 | 0 | 0 | 0 | 0 |
| *Burkholderia cepacia* | 1 | 0 | 0 | 0 | 0 |
| *Corynebacterium* spp. | 4 | 0 | 0 | 0 | 0 |
| *Enterobacter cloacae* | 1 | 0 | 0 | 0 | 0 |
| *Escherichia coli* | 1 | 0 | 0 | 0 | 0 |
| *Klebsiella pneumoniae* | 1 | 0 | 0 | 0 | 0 |
| *Micrococcus luteus* | 1 | 0 | 0 | 0 | 0 |
| *Pantoea agglomerans* | 1 | 0 | 0 | 0 | 0 |
| *Pseudomonas aeruginosa* | 3 | 0 | 0 | 0 | 0 |
| *Pseudomonas oryzihabitans* | 1 | 0 | 0 | 0 | 0 |
| *Staphylococcus epidermidis* | 5 | 2 | 2 | 2 | 2 |
| *Stenotrophomonas maltophilia* | 1 | 0 | 0 | 0 | 0 |
| *Streptococcus* spp. | 3 | 0 | 0 | 0 | 0 |

TABLE 3

Phage activity of Sa76 and Sa81 against *S. aureus* isolates

| | Sensitivity (S) or Resistance (R) of *S. aureus* Isolates | | | | | | |
|---|---|---|---|---|---|---|---|
| Phage | SPS#625 | SPS#626 | SPS#627 | SPS#628 | SPS#629 | SPS#745 | SPS#746 |
| Sa76 | S | S | R | S | R | S | R |
| Sa81 | S | S | R | S | R | S | S |

Frequency of Resistance and Complementation.

The potential for phages to complement each other in the event that bacterial resistance arises was considered as part of AB-SA01 development. Six candidate phages with broad or differing host ranges were assessed on a sensitive *S. aureus* strain. BIMs that were generated using one phage were first tested to confirm whether they truly exhibited reduced phage sensitivity after streak-purification, then cross-resistance to other phages was tested by the same method (Table 4). Sa83, Sa81, and Sa76 were similarly able to complement Sa87-induced resistance and had previously shown very similar host ranges, therefore only Sa83 was retained as part of AB-SA01. J-Sa37 more often exhibited cross-resistance than complementation and was not included in AB-SA01. J-Sa36 exhibited different complementation behavior than either Sa87 or Sa83.

TABLE 4

Complementation among candidate phages

| Phage used to generate BIM | Bacterial Lawn | BIM Confirmation[1] | Test for Complementation | | | | | |
|---|---|---|---|---|---|---|---|---|
| | | | Sa83 | Sa87 | J-Sa36 | Sa76 | Sa81 | J-Sa37 |
| Sa87 | parental | S | S | S | S | S | S | S |
| | BIM 1 | I | S | — | S | S | S | R |
| | BIM 2 | I | S | — | S | S | S | R |
| | BIM 3 | S[2] | — | — | — | — | — | — |

TABLE 4-continued

Complementation among candidate phages

| Phage used to generate BIM | Bacterial Lawn | BIM Confirmation[1] | Test for Complementation | | | | | |
|---|---|---|---|---|---|---|---|---|
| | | | Sa83 | Sa87 | J-Sa36 | Sa76 | Sa81 | J-Sa37 |
| | BIM 4 | I | S | — | S | S | S | R |
| | BIM 5 | I | S | — | I | S | S | R |
| | BIM 6 | I | S | — | S | S | S | R |
| | BIM 7 | I | S | — | S | S | S | R |
| | BIM 8 | I | S | — | I | S | S | R |
| | BIM 9 | I | S | — | I | S | S | R |
| | BIM 10 | I | S | — | I | S | S | R |
| J-Sa36 | Parental | S | S | S | S | — | — | S |
| | BIM 1 | I | S | I | — | — | — | R |
| | BIM 2 | I | I | I | — | — | — | R |
| | BIM 3 | I | I | S | — | — | — | S |
| | BIM 4 | I | I | I | — | — | — | S |

S = sensitive;
I = intermediate;
R = resistant
[1]BIM confirmation conducted using same phage as in column 1. R: resistant (no inhibition of bacterial growth), I: intermediate (phage activity seen within bacterial spot), S: sensitive (<10 colonies within bacterial spot), —: not tested
[2]BIM was not recovered during streak purification therefore concluded to be sensitive; no other testing possible After AB-SA01 composition was finalized, the mean apparent frequency of resistance to AB-SA01 was lower than the values observed for the individual phages, both at 24 h and 48 h (Table 5). However, this trend was not statistically significant (P>0.05), possibly because the values observed in this study were close to the limit of detection. This suggests that the spontaneous frequency of AB-SA01 resistance among sensitive *S. aureus* populations is no greater than about $3 \times 10^{-9}$. This number is produced by dividing the number of observed bacterial colonies by the total number of bacterial cells initially present. None of the BIM colonies observed in this study could be isolated by re-streaking on agar plates, implying that their growth on the test plates was not due to stable, heritable resistance, but was instead a temporary phenotype or a spatial phenomenon in which cells escapes contact with the phages during incubation of the phage-bacteria mixture before plating.

TABLE 5

Apparent frequency of intrinsic phage resistance in populations of *S. aureus* sensitive to AB-SA01 and its component phages

| | After 24 h plate incubation | | | After 48 h plate incubation | | |
|---|---|---|---|---|---|---|
| Phage | Replicate 1[1] | Replicate 2 | Replicate 3 | Replicate 1 | Replicate 2 | Replicate 3 |
| Sa83 | 1.1E−8 | 3.8E−9 | 5.0E−9 | 7.1E−9 | 3.8E−9 | 6.7E−9 |
| Sa87 | 2.0E−8 | 5.0E−9 | 5.0E−9 | 1.7E−8 | 5.0E−9 | 5.0E−9 |
| J-Sa36 | 2.9E−9 | 2.5E−9 | 1.2E−8 | 2.9E−9 | 1.3E−9 | 5.0E−9 |
| AB-SA01[2] | 1.4E−9 | 3.8E−9 | 3.3E−9 | 2.9E−9 | 0[3] | 3.3E−9 |

Example 2: Bacteriophage Administration to Human Patients

Bacteriophage cocktails were administered to human patients having *Staphylococcus aureus* infections that did not respond to antibiotic treatment alone. The patients were suffering from bacteremia, endocarditis (native valve), prosthetic valve endocarditis, or ventricular assist device infection.

A bacteriophage cocktail, containing approximately equal ratios of three bacteriophage, Sa87, J-Sa36, Sa83 (see U.S. Patent Pub. No. 2017/0065649, which is incorporated herein by reference in its entirety), was administered to four of the patients having *S. aureus* infections. The phage cocktail had approximately 96% coverage of *S. aureus* strains, including multidrug-resistant isolates. Susceptibility of *S. aureus* isolates from the patients was determined by soft agar overlay small drop assay prior to treatment. Patients were treated with $3 \times 10^9$ PFU of the phage cocktail via intravenous administration every 12 hours. Therapy was administered for 3 to 14 days, depending on indication. Patients were also administered the best available antibiotic therapy, as determined by the attending physician.

Results showed treatment success in 75% of patients (three) in the modified intent-to-treat population (mITT, defined as all patients who meet criteria for the clinical diagnosis, whose bacterial isolate was susceptible to AB-SA01 and who received at least one dose of AB-SA01) treated with AB-SA01 by end of therapy (determined by the treating physician as a complete resolution or significant improvement of baseline signs and symptoms). Treatment was well-tolerated and there were no treatment-related serious adverse events. All but one of the treated patients showed complete resolution or significant improvement of baseline signs and symptoms.

Ninety (90) doses of AB-SA01 was administered. Throughout the duration of treatment, the bacterial isolates from the patients remained sensitive to the cocktail.

Example 3: Bacteriophage Administration in Human Patients

Bacteriophage cocktails were administered to human patients having *S. aureus* infections that did not respond to antibiotic treatment alone. The patients were suffering from *S. aureus* infections, including bacteremia and septicemia, endocarditis (native valve), prosthetic valve endocarditis, osteomyelitis, ventricular assist device (VAD) infection, prosthetic joint infection, or chronic rhinosinusitis.

A bacteriophage composition "cocktail", containing approximately equal ratios of three bacteriophage, Sa87, J-Sa36, Sa83 (see U.S. Patent Pub. No. 2017/0065649, which is incorporated herein by reference in its entirety), was administered to fifteen (15) patients having *S. aureus* infections. The phage cocktail had approximately 96% coverage of *S. aureus* strains, including multidrug-resistant isolates. Susceptibility of *S. aureus* isolates from the patients was determined by soft agar overlay small drop assay prior to treatment. Patients were treated with $3 \times 10^9$ PFU of the phage cocktail via intravenous, intra-articular or instrasinal administration every 12 hours or once. Therapy was administered for 3 to 28 days, depending on indication. Patients were also administered the best available antibiotic therapy, as determined by the attending physician.

Results showed treatment success in 85% of patients (eleven) in the modified intent-to-treat population (mITT, defined as all patients who meet criteria for the clinical diagnosis, whose bacterial isolate was susceptible to AB-SA01 and who received at least one dose of AB-SA01) treated with AB-SA01 by end of therapy (determined by the treating physician as a complete resolution or significant improvement of baseline signs and symptoms). One patient showed improvement (7.5%) ("improvement" was determined by the treating physician as a clinically meaningful improvement of baseline signs and symptoms). One patient showed no improvement after treatment with AB-SA01 ("no improvement" was determined by the treating physician as no resolution of baseline signs and symptoms, or death).

Over 400+ doses of AB-SA01 were administered, including 300+ doses intravenously, 2 intra-articular, and 50+ intra-sinal. Treatment was well tolerated in all patients. There were no treatment-related SAEs.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the claims.

EMBODIMENTS

Embodiment 1-1. A method of treating a bacterial infection in a subject comprising administering to the subject a bacteriophage composition comprising one or more bacteriophages selected from Sa87, J-Sa36, Sa83, and mutants thereof, wherein the bacterial infection comprises *Staphylococcus*.

Embodiment 1-2. The method of embodiment 1-1, said composition comprising at least two bacteriophages selected from Sa87, J-Sa36, Sa83, or mutants thereof.

Embodiment 1-3. The method of embodiment 1-1, said composition comprising at least three bacteriophages selected from Sa87, J-Sa36, Sa83, or mutants thereof.

Embodiment 1-4. The method of embodiment 1-1, said composition comprising Sa87, J-Sa36, and Sa83, or mutants thereof.

Embodiment 1-5. The method of embodiment 1-1, said composition consisting essentially of Sa87, J-Sa36, and Sa83, or mutants thereof.

Embodiment 1-6. The method of any one of the preceding embodiments, wherein the mutant has at least 75% sequence identity across its entire genome when compared to Sa87, J-Sa36, or Sa83.

Embodiment 1-7. The method of any one of the preceding embodiments, wherein the mutant has at least 80% sequence identity across its entire genome when compared to Sa87, J-Sa36, or Sa83.

Embodiment 1-8. The method of any one of the preceding embodiments, wherein the mutant has at least 90% sequence identity across its entire genome when compared to Sa87, J-Sa36, or Sa83.

Embodiment 1-9. The method of any one of the preceding embodiments, wherein the mutant has at least 95% sequence identity across its entire genome when compared to Sa87, J-Sa36, or Sa83.

Embodiment 1-10. The bacteriophage composition according to any one of the preceding embodiments comprising one or more bacteriophages having a genomic sequence selected from: SEQ ID NO.: 1, SEQ ID NO.: 2, SEQ ID NO.: 3, and mutants thereof.

Embodiment 1-11. The bacteriophage composition according to embodiment 1-10 comprising at least two bacteriophages having a genomic sequence selected from: SEQ ID NO.: 1, SEQ ID NO.: 2, SEQ ID NO.: 3, and mutants thereof.

Embodiment 1-12. The bacteriophage composition according to embodiment 1-10 comprising three bacteriophages having a genomic sequence selected from: SEQ ID NO.: 1, SEQ ID NO.: 2, SEQ ID NO.: 3, and mutants thereof.

Embodiment 1-13. The bacteriophage composition according to any one of embodiments 1-10 to 1-12, consisting essentially of bacteriophages having a genomic sequence of: SEQ ID NO.: 1, SEQ ID NO.: 2, and SEQ ID NO.: 3, or mutants thereof.

Embodiment 1-14. The bacteriophage composition according to any one of embodiments 1-10 to 1-12, wherein the mutant has at least 75% sequence identity across its entire genome when compared to SEQ ID NO.: 1, SEQ ID NO.: 2, and/or SEQ ID NO.: 3.

Embodiment 1-15. The bacteriophage composition according to any one of embodiments 1-10 to 1-12, wherein the mutant has at least 80% sequence identity across its entire genome when compared to SEQ ID NO.: 1, SEQ ID NO.: 2, and/or SEQ ID NO.: 3.

Embodiment 1-16. The bacteriophage composition according to any one of embodiments 1-10 to 1-12, wherein the mutant has at least 90% sequence identity across its entire genome when compared to SEQ ID NO.: 1, SEQ ID NO.: 2, and/or SEQ ID NO.: 3.

Embodiment 1-17. The bacteriophage composition according to any one of embodiments 1-10 to 1-12, wherein the mutant has at least 95% sequence identity across its entire genome when compared to SEQ ID NO.: 1, SEQ ID NO.: 2, and/or SEQ ID NO.: 3.

Embodiment 1-18. The method of any one of the preceding embodiments, wherein the composition further comprises an antibiotic (e.g., a chemical antibiotic).

Embodiment 1-19. The method of embodiment 3-28, wherein the antibiotic is a fluoroquinolone, carbepenem, aminoglycoside, cephlasporin, penicillin, beta lactam, or beta lactamase inhibitor.

Embodiment 1-20. The method of any one of the preceding embodiments, wherein the composition further comprises a pharmaceutically acceptable carrier, diluent, excipient or combinations thereof.

Embodiment 1-21. The method according to embodiment 3-20, wherein the pharmaceutically acceptable carrier, diluent, excipient or combinations thereof comprises $MgSO_4$.

Embodiment 1-22. The method of any one of the preceding embodiments, wherein the bacterial infection comprises *Staphylococcus aureus*.

Embodiment 1-23. The method of any one of the preceding embodiments, further comprising administering an antibiotic (e.g., a chemical antibiotic) to the subject.

Embodiment 1-24. The method of embodiment 1-23, wherein the antibiotic is a fluoroquinolone, carbepenem, aminoglycoside, cephlasporin, penicillin, beta lactam, or beta lactamase inhibitor.

Embodiment 1-25. The method of any one of the preceding embodiments, wherein the bacterial infection is an infection characterized by the presence of a bacterial biofilm.

Embodiment 1-26. The method of any one of the preceding embodiments, wherein the bacterial infection is not a pulmonary infection.

Embodiment 1-27. The method of any one of the preceding embodiments, wherein the bacterial infection is rhinosinusitis, urinary tract infection, intra-abdominal infection, skin infection, skin structure infection, bacteremia, endocarditis, or an implant infection.

Embodiment 1-28. The method or embodiment 1-27, wherein the implant infection is a cardiac implant infection (e.g., ventricular assist device infection, pacemaker infection), prosthetic joint infection, or prosthetic valve endocarditis.

Embodiment 1-29. The method of any one of the preceding embodiments, wherein the bacterial infection is resistant to antibiotics.

Embodiment 1-30. The method of any one of the preceding embodiments, wherein the composition is administered via an aerosolized formulation of the composition.

Embodiment 1-31. The method of any one of embodiments 1-22 to 1-30, wherein the composition is administered intravenously.

Embodiment 1-32. A bacteriophage composition comprising one or more bacteriophages selected from Sa87, J-Sa36, Sa83, and mutants thereof, and a cryoprotectant.

Embodiment 1-33. A bacteriophage composition comprising one or more bacteriophages selected from bacteriophages having a genomic sequence selected from: SEQ ID NO.: 1, SEQ ID NO.: 2, SEQ ID NO.: 3, and mutants thereof, and a cryoprotectant.

Embodiment 1-34. The bacteriophage composition of embodiment 1-32 or 1-33, wherein the cryoprotectant comprises glycerol.

Embodiment 1-35. The composition or method of any one of the preceding embodiments, wherein the bacteriophage of the composition infect and lyse *Staphylococcus*.

Embodiment 1-36. The composition or method of any one of the preceding embodiments, wherein the bacteriophage of the composition infect and lyse *Staphylococcus aureus*.

Embodiment 1-37. The composition or method of any one of the preceding embodiments, wherein the bacteriophage of the composition infect and lyse methicillin-resistant *Staphylococcus aureus*.

SEQUENCE LISTING

The patent contains a lengthy sequence listing. A copy of the sequence listing is available in electronic form from the USPTO web site (https://seqdata.uspto.gov/?pageRequest=docDetail&DocID=US11654166B2). An electronic copy of the sequence listing will also be available from the USPTO upon request and payment of the fee set forth in 37 CFR 1.19(b)(3).

The invention claimed is:

1. A bacteriophage composition substantially free of bacterial components comprising two or more obligately lytic bacteriophages, wherein at least one of the bacteriophages comprises a nucleotide sequence having at least 90% identity to any one of SEQ ID NO: 1, SEQ ID NO: 2, or SEQ ID NO: 3.

2. The bacteriophage composition of claim 1, wherein the composition's target bacteria range is broader than the range of any individual bacteriophage in the composition.

3. The bacteriophage composition of claim 1, where the composition comprises at least one bacteriophage comprising a nucleotide sequence having at least 90% identity to any one of SEQ ID NO: 1, SEQ ID NO: 2, or SEQ ID NO: 3; and at least one additional bacteriophage.

4. The composition of claim 1, wherein the composition is substantially free of bacterial endotoxin.

5. The composition of claim 1, wherein the bacterial composition is substantially free of bacterial host protein.

6. The composition of claim 1, wherein the composition further comprises a pharmaceutically acceptable excipient, diluent, or carrier, or combinations thereof.

7. The composition of claim 6, wherein the pharmaceutically acceptable carrier, diluent, excipient or combinations thereof comprises calcium salt or magnesium salt.

8. The composition of claim 1, wherein the composition is a liquid, semi-liquid, solid, frozen, or lyophilized formulation.

9. The composition of claim 1, wherein the two or more bacteriophages infect and lyse methicillin-resistant *Staphylococcus aureus* or methicillin-sensitive *Staphylococcus aureus*.

10. The composition of claim 1, wherein the composition comprises between $1 \times 10^5$ and $1 \times 10^{11}$ PFU of each bacteriophage.

11. The composition of claim 1, wherein the composition is to be administered at a dosage of $1 \times 10^9$ to $3 \times 10^{11}$ total PFU per milliliter.

12. The composition of claim 1, wherein the composition is stored at 2-8° C. or at room temperature.

13. The composition of claim 1, wherein the nucleotide sequence of at least one bacteriophage in the composition is not naturally-occurring.

14. The composition of claim 1, wherein the composition comprises two or more bacteriophages, wherein the two or more bacteriophages individually comprise a nucleotide sequence having at least 90% identity to SEQ ID NO: 1, SEQ ID NO: 2, or SEQ ID NO: 3.

15. The composition of claim 1, wherein the obligately lytic bacteriophages are capable of complementation.

16. A bacteriophage composition substantially free of bacterial components comprising one or more obligately lytic bacteriophages and a storage medium for storage at a temperature at or below 8° C., wherein the bacteriophage comprises a nucleotide sequence having at least 90% identity to any one of SEQ ID NO: 1, SEQ ID NO: 2, or SEQ ID NO: 3, wherein each individual bacteriophage is not prone to generalized transduction and does not carry an antibiotic resistance gene.

17. The bacteriophage composition of claim 16, wherein the storage medium comprises a cryoprotectant.

18. The bacteriophage composition of claim 17, wherein the cryoprotectant comprises glycerol or sucrose.

19. The bacteriophage composition of claim 18, wherein the glycerol is in a concentration of about 5% to about 30% (v/v) and the sucrose is in a concentration of about 10% (v/v).

20. The bacteriophage composition of claim 16, wherein the composition is substantially free of bacterial endotoxin.

21. The composition of claim 16, wherein the composition is substantially free of bacterial host protein.

22. The composition of claim 16, wherein the composition further comprises a pharmaceutically acceptable excipient, diluent, or carrier, or combinations thereof.

23. The composition of claim 22, wherein the pharmaceutically acceptable carrier, diluent, excipient or combinations thereof comprises calcium salt or magnesium salt.

24. The composition of claim 16, wherein the composition is a liquid, semi-liquid, solid, frozen, or lyophilized formulation.

25. The composition of claim 16, wherein the bacteriophages of the composition infect and lyse methicillin-resistant *Staphylococcus aureus* or methicillin-sensitive *Staphylococcus aureus*.

26. The composition of claim 16, wherein the composition comprises between $1 \times 10^5$ and $1 \times 10^{11}$ PFU of each bacteriophage.

27. The composition of claim 16, wherein the composition is to be administered at a dosage ranging between $1 \times 10^9$ PFU and $3 \times 10^{11}$ total PFU per milliliter.

28. The composition of claim 16, wherein the composition is stored at 2-8° C. or at room temperature.

29. The composition of claim 16, wherein the nucleotide sequence of at least one bacteriophage is not naturally-occurring.

30. The bacteriophage composition of claim 16, wherein the bacteriophage comprises a nucleotide sequence having at least 93% identity to any one of SEQ ID NO: 1, SEQ ID NO: 2, or SEQ ID NO: 3.

31. A bacteriophage composition substantially free of bacterial components comprising one or more obligately lytic bacteriophages, wherein the bacteriophage comprises a nucleotide sequence having at least 90% but not 100% identity to any one of SEQ ID NO: 1, SEQ ID NO: 2, or SEQ ID NO: 3, wherein each individual bacteriophage is not prone to generalized transduction and does not carry an antibiotic resistance gene.

32. The bacteriophage composition of claim 31, wherein the bacteriophage comprises a nucleotide sequence having at least 93% identity to any one of SEQ ID NO: 1, SEQ ID NO: 2, or SEQ ID NO: 3.

33. A bacteriophage composition substantially free of bacterial components comprising one or more non-naturally occurring, obligately lytic bacteriophages, wherein at least one of the bacteriophages comprises a nucleotide sequence having at least 90% identity to any one of SEQ ID NO: 1, SEQ ID NO: 2, or SEQ ID NO: 3; wherein each individual bacteriophage is not prone to generalized transduction and does not carry an antibiotic resistance gene.

34. The composition of claim 33, wherein the obligately lytic bacteriophages are capable of complementation.

* * * * *